United States Patent
Rey

(10) Patent No.: US 10,179,939 B2
(45) Date of Patent: *Jan. 15, 2019

(54) GROWTH-INDEPENDENT DETECTION OF CELLS

(71) Applicant: GeneWeave Biosciences, Inc., Los Gatos, CA (US)

(72) Inventor: Diego Ariel Rey, San Francisco, CA (US)

(73) Assignee: GeneWeave Biosciences, Inc., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/364,095

(22) Filed: Nov. 29, 2016

(65) Prior Publication Data

US 2017/0137898 A1 May 18, 2017

Related U.S. Application Data

(63) Continuation of application No. PCT/US2015/035611, filed on Jun. 12, 2015.

(60) Provisional application No. 62/011,660, filed on Jun. 13, 2014.

(51) Int. Cl.
| | | |
|---|---|---|
| *C12N 1/20* | (2006.01) | |
| *C12Q 1/6897* | (2018.01) | |
| *C12Q 1/04* | (2006.01) | |
| *C12Q 1/14* | (2006.01) | |

(52) U.S. Cl.
CPC .......... *C12Q 1/6897* (2013.01); *C12Q 1/04* (2013.01); *C12Q 1/14* (2013.01)

(58) Field of Classification Search
CPC . C12N 1/20; C12N 7/00; C12N 15/70; C12N 15/74; C12Q 1/14; C12Q 1/18; C12Q 1/66; C12Q 1/68

USPC ................. 435/5, 6.14, 320.1, 456
See application file for complete search history.

(56) References Cited

U.S. PATENT DOCUMENTS

| | | | |
|---|---|---|---|
| 8,829,473 B1 | 9/2014 | Griswold et al. | |
| 2007/0178450 A1* | 8/2007 | Wheeler | C12Q 1/06 435/5 |
| 2009/0155768 A1* | 6/2009 | Scholl | C12N 15/70 435/5 |
| 2010/0112549 A1 | 5/2010 | Rey et al. | |
| 2014/0272928 A1 | 9/2014 | Rey et al. | |
| 2014/0278136 A1 | 9/2014 | Shamsheyeva et al. | |
| 2015/0064138 A1 | 3/2015 | Lu et al. | |

(Continued)

FOREIGN PATENT DOCUMENTS

WO 2014160418 A2 10/2014

OTHER PUBLICATIONS

Schofield et al., Bacteriophage. Apr. 1, 2012; 2(2): 105-283. (Year: 2012).*

(Continued)

*Primary Examiner* — Jana A Hines
(74) *Attorney, Agent, or Firm* — David J. Chang

(57) ABSTRACT

Disclosed herein are various methods, systems, and compositions for the growth independent detection of cells such as microorganisms including bacteria. While existing cellular detection methodologies benefit from cell growth, the methods, systems, and compositions disclosed herein demonstrate embodiments that are independent of cell growth while still allowing for cell-based detection.

11 Claims, 2 Drawing Sheets
Specification includes a Sequence Listing.

(56) References Cited

U.S. PATENT DOCUMENTS

2015/0104787 A1    4/2015    Rey et al.
2015/0218613 A1    8/2015    DeForest et al.

OTHER PUBLICATIONS

Dusthackeer et al. J Microbiol Methods. Apr. 2008;73(1):18-25. doi: 10.1016/j.mimet.2008.01.005. Epub Jan. 19, 2008.*
Dusthackeer A. et al., "Construction and evaluation of luciferase reporter phages for the detection of active and non-replicating tubercle bacilli", J. Microbial. Methods, 2008, 73, pp. 18-25.
Extended European Search Report EP Application No. 15806348.7, dated Dec. 15, 2017.
Ubeda, C. et al., "Specificity of staphylococcal phage and SaPI DNA packaging as revealed by integrase and terminase mutations", 2009, Molecular Microbiology, 72(1):98-108.

* cited by examiner

SEQUENCE LISTING

<160> NUMBER OF SEQ ID NOS: 5

<210> SEQ ID NO 1
<211> LENGTH: 4681
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (301)..(301)
<223> OTHER INFORMATION: a, c, t, g, unknown or other
<220> FEATURE:
<221> NAME/KEY: modified_base
<222> LOCATION: (4056)..(4056)
<223> OTHER INFORMATION: a, c, t, g, unknown or other

<400> SEQUENCE: 1
tttgcggaaa gagttagtaa gttaacagaa gacgagccaa acctaaatgg tttagcagga    60
aacttagata aaaaaatgaa tccagaatta tattcagaac aggaacagca acaagagcaa   120

```
caaaagaatc aaaaacgaga tagaggtatg cacttataga acatgcattt atgccgagaa      180
aacttattgg ttggaatggg ctatgtgtta gctaacttgt tagcgagttg gttggacttg      240
aattgggatt aatcccaaga aagtaccggc tcaacaaccc ataaagccct gtaggttccg      300
nccaataagg aaattggaat aaagcaataa aaggagttga agaaatgaaa ttcagagaag      360
cctttgagaa ttttataaca agtaagtatg tacttggtgt tttagtagtc ttaactgttt      420
accagataat acaaatgctt aaataaaaaa agacttgatc tgattagacc aaatcttttg      480
atagtgttat attaataaca aaataaaaag gagtcgctca cgccctacca aagtttgtga      540
acgacatcat tcaaagaaaa aaacactgag ttgtttttat aatcttgtat atttagatat      600
taaacgatat ttaaatatac atcaagatat atatttgggt gagcgattac ttaaacgaaa      660
ttgagattaa ggagtcgatt ttttatgtat aaaaacaatc atgcaaatca ttcaaatcat      720
ttggaaaatc acgatttaga caatttttct aaaaccggct actctaatag ccggttggac      780
gcacatactg tgtgcatatc tgatccaaaa ttaagttttg atgcaatgac gatcgttgga      840
aatctcaacc gagacaacgc tcaggcccct tctaaattta tgagtgtaga gccccaaata      900
agactttggg atattcttca aacaaagttt aaagctaaag cacttcaaga aaaagtttat      960
attgaatatg acaaagtgaa agcagatagt tgggatagac gtaatatgcg tattgaattt     1020
aatccaaaca aacttacacg agatgaaatg atttggttaa aacaaaatat aataagctac     1080
atggaagatg acgttttac aagattagat ttagcctttg attttgaaga tgatttgagt     1140
gactactatg caatgtctga taaagcagtt aagaaaacta ttttttatgg tcgtaatggt     1200
aagccagaaa caaatatttt tggcgtgaga gatagtaata gatttattag aatttataat     1260
aaaaagcaag aacgtaaaga taatgcagat gctgaagtta tgtctgaaca tttatggcgt     1320
gtagaaatcg aacttaaaag agatatggtg gattactgga atgattgctt tagtgattta     1380
catatcttgc aaccagattg gaaaactatc caacgcactg cggatagagc aatagttttt     1440
atgttattga gtgatgaaga agaatgggga agcttcaca gaaattctag aacaaaatat     1500
aagaatttga taaagaaat ttcgccagtc gatttaacgg acttaatgaa atcgacttta     1560
aaagcgaacg aaaaacaatt gcaaaaacaa atcgattttt ggcaacatga atttaaattt     1620
tggaaatagt gtacatatta atattactga acaaaaatga tatatttaaa ctattctaat     1680
ttaggaggat ttttttatga agtgtctatt taaaaatttg gggaatttat atgaggtgaa     1740
agaataattt acccctataa actttagcca cctcaagtaa agaggtaaaa ttgtttagtt     1800
tatataaaaa atttaaaggt ttgttttata gcgttttatt ttggctttgt attctttcat     1860
tttttagtgt attaaatgaa atggttttaa atgtttcttt acctgatatt gcaaatcatt     1920
ttaatactac tcctggaatt acaaactggg taaacactgc atatatgtta acttttttcga     1980
taggaacagc agtatatgga aaattatctg attatataaa tataaaaaaa ttgttaatta     2040
ttggtattag tttgagctgt cttggttcat tgattgcttt tattgggccc acctaggcaa     2100
atatgctctt acgtgctatt atttaagtga ctatttaaaa ggagttaata aatatgcggc     2160
aaggtattct taaataaact gtcaatttga tagcgggaac aaataattag atgtcctttt     2220
ttaggagggc ttagtttttt gtacccagtt taagaatacc tttatcatgt gattctaaag     2280
tatccagaga atatctgtat gctttgtata cctatggtta tgcataaaaa tcccagtgat     2340
aaaagtattt atcactggga tttttatgcc cttttgggtt tttgaatgga ggaaaatcac     2400
atgaaaatta ttaatattgg agttttagct catgttgatg caggaaaaac taccttaaca     2460
gaaagcttat tatataacag tggagcgatt acagaattag gaagcgtgga caaaggtaca     2520
```

```
acgaggacgg ataatacgct tttagaacgt cagagaggaa ttacaattca gacaggaata    2580
acctctttc agtgggaaaa tacgaaggtg aacatcatag acacgccagg acatatggat    2640
ttcttagcag aagtatatcg ttcattatca gttttagatg gggcaattct actgatttct    2700
gcaaaagatg gcgtacaagc acaaactcgt atattatttc atgcacttag aaaatggggg   2760
attcccacaa tctttttat caataagatt gaccaaaatg gaattgattt atcaacggtt    2820
tatcaggata ttaaagagaa actttctgcc gaaattgtaa tcaaacagaa ggtagaactg    2880
tatcctaata tgtgtgtgac gaactttacc gaatctgaac aatgggatac ggtaatagag    2940
ggaaacgata acctttaga gaaatatatg tccggtaaat cattagaagc attggaactc     3000
gaacaagagg aaagcataag atttcagaat tgttctctgt tccctctta tcatggaagt     3060
gcaaaaagta atatagggat tgataaccctt atagaagtta ttactaataa atttatttca    3120
tcaacacatc gaggtccgtc tgaactttgc ggaaatgttt tcaaaattga atatacaaaa    3180
aaaagacaac gtcttgcata tatcgccctt tatagtggag tactcactt acgagattcg     3240
gttagagtat cagaaaaaga aaaataaaa gttacagaaa tgtatacttc aataaatggt     3300
gaattatgta agattgatag agcttattct ggagaaattg ttatttttgca aaatgagttt   3360
ttgaagttaa atagtgttct tggagataca aaactattgc cacagagaaa aaagattgaa    3420
aatccgcacc ctctactaca aacaactgtt gaaccgagta aacctgaaca gagagaaatg    3480
ttgcttgatg cccttttgga aatctcagat agtgatccgc ttctacgata ttacgtggat    3540
tctacgacac atgaaattat actttctttc ttagggaaag tacaaatgga agtgattagt    3600
gcactgttgc aagaaaagta tcatgtggag atagaactaa aagagcctac agtcatttat   3660
atggagagac cgttaaaaaa tgcagaatat accattcaca tcgaagtgcc gccaaatcct   3720
ttctgggctt ccattggttt atctgtatca ccgcttccgt tgggaagtgg aatgcagtat   3780
gagagctcgg tttctcttgg atacttaaat caatcatttc aaaatgcagt tatggaaggg   3840
gtacgctatg gttgcgaaca aggattatat ggttggaatg tgacggattg taaaatctgt   3900
tttaagtacg gtttatacta tagccctgtt agtactccag cagattttcg gatgcttact   3960
cctattgtac tggagcaagc ctttagaaaa gctggaacag aattgttaga gccatatctt   4020
agttttaaag tttatgcacc acaggaatat ctttcncggg catataacga tgctcccaaa   4080
tattgtgcaa atatcgtaaa tactcaactg aaaaataatg aggtcattat tattggagaa   4140
attcctgctc gatgtattca agattatcgc aatgatttaa cttttttac aaatgggctt   4200
agtgttgtt tagcagagct aaaaggatat caggttacca ctggcgaacc tgtttgccag   4260
acccgtcgtc taaatagtcg gatagataaa gtaagatata tgttcaataa aataacttag   4320
tgcgtttttat gttgttatat aaatatggtt tcttattaaa taagatgaaa tattctttaa   4380
tatagatttg aattaaagtg gaaaggagga gattgttatt ataaactaca agtggatatt   4440
gtgtcctatt tgtggaaata aaacaagact acgaatacga gtggatacta tacttaaaaa   4500
tttcccttta tacagcccca aatgtaagaa cgaaacttta attaatgttc aaaaaatgaa   4560
tataataaca atcaaagagc cagacgccaa gacgcagagc cgataatttg agaaatgaaa   4620
ctctcatctt atcggctctt tttgtttatc tgaattttac tgactagcct tcaatatttc   4680
c                                                                    4681
```

<210> SEQ ID NO 2
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | | |
|---|---|---|---|---|---|
| gtctagttaa | tgtgtaacgt | aacattagct | agattttttt | attcaaaaaa | atatttacaa | 60 |
| atattaggaa | atttaagtgt | aaaagagttg | ataaatgatt | atattgggac | tataatataa | 120 |
| ttaaggtc | | | | | | 128 |

<210> SEQ ID NO 3
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | | | | | |
|---|---|---|---|---|---|
| aattggcagt | aaagtggcag | ttttgatac | ctaaaatgag | atattatgat | agtgtaggat | 60 |
| attgactatc | ttactgcgtt | tcccttatcg | caattaggaa | taaaggatct | atgtgggttg | 120 |
| gctgattata | gccaatcctt | ttttaatttt | aaaaagcgta | tagcgcgaga | gttggtggta | 180 |
| aatgaaatga | acgaaaaaca | aaagagattc | gcagatgaat | atataatgaa | tggatgtaat | 240 |
| ggtaaaaaag | cagcaatttc | agcaggttat | agtaagaaaa | cagcagagtc | tttagcaagt | 300 |
| cgattgttaa | gaaatgttaa | tgtttcggaa | tatattaaag | aacgattaga | acagatacaa | 360 |
| gaagagcgtt | taatgagcat | tacagaagct | ttagcgttat | ctgcttctat | tgctagagga | 420 |
| gaacctcaag | aggcttacag | taagaaatat | gaccatttaa | acgatgaagt | ggaaaaagag | 480 |
| gttacttaca | caatcacacc | aactttttgaa | gagcgtcaga | gatctattga | ccacatacta | 540 |
| aaagttcatg | gtgcgtatat | cgacaaaaaa | gaaattactc | agaagaatat | tgagattaat | 600 |
| attggtgagt | acgatgacga | aagttaaatt | aaactttaac | aaaccatcta | atgttttcaa | 660 |
| cag | | | | | | 663 |

<210> SEQ ID NO 4
<211> LENGTH: 2769
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | | | | | |
|---|---|---|---|---|---|
| attagacaac | aaacaagtca | ttgaaaattc | cgacttatta | ttcaaaaaga | aatttgatag | 60 |
| cgcagatata | caagctaggt | taaaagtagg | cgataaggta | gaagttaaaa | caatcggtta | 120 |
| tagaatacac | tttttaaatt | tatatccggt | cttatacgaa | gtaaagaagg | tagataaaca | 180 |
| atgattaaac | aaatactaag | actattattc | ttactagcaa | tgtatgagtt | aggtaagtat | 240 |
| gtaactgagc | aagtatatat | tatgatgacg | gctaatgatg | atgtagaggt | gccgagtgac | 300 |
| ttcgcgaagt | tgagcgatca | gtcagatttg | atgagggcgg | aggtgacgga | gtagatgatg | 360 |
| tggttagtca | tagcaattat | attactagtc | atcttattgt | ttggtgtgat | gttgcaagct | 420 |
| gaacagttaa | aaggcgatgt | gaaagttaaa | gagcgggaga | tagagatatt | aagaagtaga | 480 |
| ttgagacatt | ttgaagatta | aaaatatttg | tatggagggt | attcatgact | aaaaagaaat | 540 |
| atggattaaa | attatcaaca | gttcgaaagt | tagaagatga | gttgtgtgat | tatcctaatt | 600 |
| atcataagca | actcgaagat | ttaagaagtg | aaataatgac | accatggatt | ccaacagata | 660 |

```
caaatatagg cggggagttt gtaccgtcta atacatcgaa acagaaatg gcagtaacta     720 attatctttg tagtatacga agaggtaaaa tccttgagtt taagagcgct attgaacgta     780
taatcaacac atcaagtagg aaagaacgcg aattcattca agagtattat tttaataaaa     840
aggaattagt gaaagtttgt gatgacatac acatttctga tagaactgct catagaatca     900
aaaggaaaat catatctaga ttggcggaag agttaggga agagtgaaat tggcagtaaa     960
gtggcagttt ttgataccta aaatgagata ttatgatagt gtaggatatt gactatctta    1020
ctgcgtttcc cttatcgcaa ttaggaataa aggatctatg tgggttggct gattatagcc    1080
aatccttttt taattttaaa aagcgtatag cgcgagagtt ggtggtaaat gaaatgaacg    1140
aaaaacaaaa gagattcgca gatgaatata taatgaatgg atgtaatggt aaaaaagcag    1200
caatttcagc aggttatagt aagaaaacag cagagtcttt agcaagtcga ttgttaagaa    1260
atgttaatgt ttcggaatat attaaagaac gattagaaca gatacaagaa gagcgtttaa    1320
tgagcattac agaagcttta gcgttatctg cttctattgc tagaggagaa cctcaagagg    1380
cttacagtaa gaaatatgac catttaaacg atgaagtgga aaaagaggtt acttacacaa    1440
tcacaccaac ttttgaagag cgtcagagat ctattgacca catactaaaa gttcatggtg    1500
cgtatatcga caaaaaagaa attactcaga agaaattga gattaatatt ggtgagtacg    1560
atgacgaaag ttaaattaaa ctttaacaaa ccatctaatg ttttcaacag aaacatattc    1620
gaaatactaa ccaattacga taacttcact gaagtacatt acggtggagg ttcgagtggt    1680
aagtctcacg gcgttataca aaaagttgta cttaaagcat tgcaagactg gaaatatcct    1740
aggcgtatac tatggcttag aaaagtccaa tcaacaatta aagatagttt attcgaagat    1800
gtcaaagatt gtttgataaa cttcggtatt tgggacatgt gcctttggaa taagactgat    1860
aacaaagttg aattgccaaa cggcgcagtt tttttgttta aaggattaga taacccagag    1920
aaaataaagt cgataaaagg catatcagac atagtcatgg aagaagcgtc tgaattcaca    1980
ctaaatgatt acacgcaatt aacgttgcgt ttgagggagc gtaaacacgt gaataagcaa    2040
atatttttga tgtttaaccc agtatctaaa ctgaattggg tttataagta tttctttgaa    2100
catggtgaac caatggaaaa tgtcatgatt agacaatcta gttatcgaga taataagttt    2160
cttgatgaaa tgacacgaca aaacttagag ttgttagcaa atcgtaatcc agcatattac    2220
aaaatttatg cgttaggtga attttctaca ctagacaaat tggttttccc taagtatgaa    2280
aaacgtttaa taaataaga tgagttaaga catttacctt cttattttgg attggacttt    2340
ggctacgtta atgatcctag tgcttttata cattctaaaa tagatgtaaa gaaaagaag    2400 ttatacatca ttgaagagta tgttaaacaa ggtatgctga atgatgaaat agctaatgtc    2460
ataaagcaac ttggttatgc taaagaagaa attacagcag atagtgcaga acaaaaaagt    2520
atagctgaat taaggaatct agggcttaaa aggattttac caaccaaaaa agggaagggc    2580
tcggttgtac aagggttaca attcttaatg caatttgaaa tcattgttga tgaacgttgt    2640
ttcaagacta ttgaagagtt tgacaactac acatggcaaa aggacaaaga tacaggtgaa    2700
tataccaatg aaccagtaga tacatacaat cattgtatcg attcgttgcg ttattcagtg    2760
gaacgattc                                                            2769

<210> SEQ ID NO 5
<211> LENGTH: 10319
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 5

```
ggcgccatgg ttaagggccc tttgcggaaa gagttagtaa gttaacagaa gacgaaccaa    60
aactaaatgg tttagcagga aacttagata aaaaaatgaa tccagaatta tattcagaac   120
aggaacagca acaagaacaa caaaagaatc aaaaacgaga tagaggtatg cacttataga   180
acatgcattt atgccgagaa aacttattgg ttggaatggg ctatgtgtta gctaacttgt   240
tagcgagttg gttggacttg aattgggatt aatcccaaga aagtaccaac tcaacaacac   300
ataaagcccT gtaggttccg accaataagg aaattggaat aaagcaataa aaggagttga   360
agaaatgaaa ttcagagaag cctttgagaa ttttataaca agtaagtatg tacttggtgt   420
tttagtagtc ttaactgttt accagataat acaaatgctt aaataaaaaa agacttgatc   480
tgattagacc aaatcttttg atagtgttat attaataaca aaataaaaag gagtcgctca   540
cgccctacca aagtttgtga acgacatcat tcaaagaaaa aaacactgag ttgttttat   600
aatcttgtat atttagatat taaacgatat ttaaatatac atcaagatat atatttgggt   660
gagcgattac ttaaacgaaa ttgagattaa ggagtcgatt ttttatgtat aaaaacaatc   720
atgcaaatca ttcaaatcat ttggaaaatc acgatttaga caattttttct aaaaccggct   780
actctaatag ccggttggac gcacatactg tgtgcatatc tgatccaaaa ttaagttttg   840
atgcaatgac gatcgttgga aatctcaacc gagacaacgc tcaggcccct tctaaattta   900
tgagtgtaga gccccaaata agactttggg atattcttca aacaaagttt aaagctaaag   960
cacttcaaga aaaagtttat attgaatatg acaaagtgaa agcagatagt tgggatagac  1020
gtaatatgcg tattgaattt aatccaaaca aacttacacg agatgaaatg atttggttaa  1080
aacaaaatat aataagctac atggaagatg acggttttac aagattagat ttagcctttg  1140
attttgaaga tgattttgagt gactactatg caatgtctga taaagcagtt aagaaaacta  1200
ttttttatgg tcgtaatggt aagccagaaa caaaatattt tggcgtgaga gatagtaata  1260
gatttattag aatttataat aaaaagcaag aacgtaaaga taatgcagat gctgaagtta  1320
tgtctgaaca tttatggcgt gtagaaatcg aacttaaaag agatatggtg gattactgga  1380
atgattgctt tagtgattta catatcttgc aaccagattg gaaaactatc caacgcactg  1440
cggatagagc aatagttttt atgttattga gtgatgaaga agaatgggga aagcttcaca  1500
gaaattctag aacaaatat aagaatttga taaagaaat ttcgccagtc gatttaacgg  1560
acttaatgaa atcgacttta aaagcgaacg aaaaacaatt gcaaaacaa atcgatttt  1620
ggcaacatga atttaaattt tggaaatagt gtacatatta atattactga acaaaaatga  1680
tatatttaaa ctattctaat ttaggaggat tttttatga agtgtctatt taaaaatttg  1740
gggaatttat atgaggtgaa agaataattt accctataa actttagcca cctcaagtaa  1800
agaggtaaaa ttgtttagtt tatataaaaa atttaaaggt ttgttttata gcgttttatt  1860
ttggctttgt attctttcat tttttagtgt attaaatgaa atggttttaa atgtttcttt  1920
acctgatatt gcaaatcatt ttaatactac tcctggaatt acaaactggg taaacactgc  1980
atatatgtta acttttttcga taggaacagc agtatatgga aaattatctg attatataaa  2040
tataaaaaaa ttgttaatta ttggtattag tttgagctgt cttggttcat tgattgcttt  2100
tattgggccc acctaggcaa atatgctctt acgtgctatt atttaagtga ctatttaaaa  2160
ggagttaata aatatgcggc aaggtattct taaataaact gtcaatttga tagcgggaac  2220
```

-continued

```
aaataattag atgtccttttt ttaggagggc ttagtttttt gtacccagtt taagaatacc    2280
tttatcatgt gattctaaag tatccagaga atatctgtat gctttgtata cctatggtta    2340
tgcataaaaa tcccagtgat aaaagtattt atcactggga ttttatgcc cttttgggtt    2400 tttgaatgga ggaaaatcac atgaaaatta ttaatattgg agttttagct catgttgatg    2460
caggaaaaac taccttaaca gaaagcttat tatataacag tggagcgatt acagaattag    2520
gaagcgtgga caaggtaca acgaggacgg ataatacgct tttagaacgt cagagaggaa    2580
ttacaattca gacaggaata acctctttc agtgggaaaa tacgaaggtg aacatcatag    2640
acacgccagg acatatggat ttcttagcag aagtatatcg ttcattatca gttttagatg    2700
gggcaattct actgatttct gcaaaagatg gcgtacaagc acaaactcgt atattatttc    2760
atgcacttag gaaaatgggg attcccacaa tcttttttat caataagatt gaccaaaatg    2820
gaattgattt atcaacggtt tatcaggata ttaaagagaa actttctgcc gaaattgtaa    2880
tcaaacagaa ggtagaactg tatcctaata tgtgtgtgac gaactttacc gaatctgaac    2940
aatgggatac ggtaatagag ggaaacgata acctttaga gaaatatatg tccggtaaat    3000
cattagaagc attggaactc gaacaagagg aaagcataag atttcagaat tgttctctgt    3060 tccctctta tcatggaagt gcaaaagta atataggat tgataacctt atagaagtta    3120
ttactaataa attttattca tcaacacatc gaggtccgtc tgaactttgc ggaaatgttt    3180
tcaaaattga atatacaaaa aaagacaac gtcttgcata tacgccctt tatagtggag    3240 tactacattt acgagattcg gttagagtat cagaaaaaga aaaataaaa gttacagaaa    3300 tgtatacttc aataaatggt gaattatgta agattgatag agcttattct ggagaaattg    3360
ttattttgca aaatgagttt ttgaagttaa atagtgttct tggagataca aaactattgc    3420
cacagagaaa aagattgaa atccgcacc ctctactaca aacaactgtt gaaccgagta    3480
aacctgaaca gagagaaatg ttgcttgatg cccttttgga aatctcagat agtgatccgc    3540
ttctacgata ttacgtggat tctacgacac atgaaattat actttcttc ttagggaaag    3600 tacaaatgga agtgattagt gcactgttgc aagaaaagta tcatgtggag atagaactaa    3660
aagagcctac agtcatttat atggagagac cgttaaaaaa tgcagaatat accattcaca    3720
tcgaagtgcc gccaaatcct ttctgggctt ccattggttt atctgtatcg ccgcttccgt    3780
tgggaagtgg aatgcagtat gagagctcgg tttctcttgg atacttaaat caatcatttc    3840
aaaatgcagt tatggaaggg gtacgctatg gttgcgaaca aggattatat ggttggaatg    3900
tgacggattg taaatctgt tttaagtacg gttttatacta tagccctgtt agtactccag    3960
cagattttcg gatgcttact cctattgtac tggagcaagc ctttagaaaa gctggaacag    4020
aattgttaga gccatatctt agtttttaaag tttatgcacc acaggaatat cttcacggg    4080 catataacga tgctcccaaa tattgtgcaa atatcgtaaa tactcaactg aaaaataatg    4140
aggtcattat tattggagaa attcctgctc gatgtattca agattatcgc aatgatttaa    4200
ctttttttac aaatgggctt agtgtttgtt tagcagagct aaaaggatat caggttacca    4260
ctggcgaacc tgtttgccag acccgtcgtc taaatagtcg atagataaa gtaagatata    4320 tgttcaataa aataacttag tgcgttttat gttgttatat aaatatggtt tcttattaaa    4380
taagatgaaa tattctttaa tatagatttg aattaaagtg gaaggagga gattgttatt    4440 ataaactaca agtggatatt gtgtcctagt tgtggaaata aaacaagact acgaatacga    4500
gtggatacta tacttaaaa tttccctta tacagcccca aatgtaagaa cgaaacttta    4560
attaatgttc aaaaaatgaa tataataaca atcaaagagc cagacgccaa gacgcagagc    4620
```

```
cgataatttg agaaatgaaa ctctcatctt atcggctctt tttgtttatc tgaattttac    4680
tgactagcct tcaatatttc cgcggccagc ttactatgcc attattaagc ttgtaatatc    4740
ggagggttta ttaattggca gtaaagtggc agttttgat accttaaatg agatattatg    4800
atagtgtagg atattgacta tcgtactgcg tttccctacc gcaaattagg aataaaggat    4860
ctatgtgggt tggctgatta tagccaatcc ttttttaatt ttaaaaagcg tatagcgcga    4920
gagttggtgg taaatgaaat gaacgaaaaa caaagagat tcgcagatga atatataatg    4980
aatggatgta atggtaaaaa agcagcaatt acagtaggtt atagtaagaa acagcagag    5040 tctttagcaa gtcgattgtt aagaaatgtt aatgtttcgg aatatattaa agaacgatta    5100
gaacaggtac aagaagagcg tttaatgagt attacagaag ctttagcgtt atctgcttct    5160
attgctagag gagaacctca agaggcttac agtaagaaat atgaccattt aaacgatgaa    5220
gtggaaaaag aggttactta cacaatcaca ccaactttg aagagcgtca gagatctatt    5280
gaccacatac taaaagtaca tggtgcgtat atcgataaaa aagaaattac tcagaagaat    5340
attgagatta atattggtga gtacgatgac gaaagttaaa ttgaacttta acaaaccgtc    5400
taatgttttc aatagccgcg ggggcccaac acaccaactt tgaagagcg tcagagatct    5460 attgaccaca tactaaaagt acatggtgcg tatatcgata aaaagaaat tactcagaag    5520 aatattgaga ttaatattgg tgagtacgat gacgaaagtt aaattaaact ttaacaaacc    5580
gtctaatgtt ttcaatagcc gcgggggccc aacgagcggc cgcatagtta agccagcccc    5640
gacacccgcc aacacccgct gacgcgccct gacgggcttg tctgctcccg gcatccgctt    5700
acagacaagc tgtgaccgtc tccgggagct gcatgtgtca gaggttttca ccgtcatcac    5760
cgaaacgcgc gagacgaaag ggcctcgtga tacgcctatt tttataggtt aatgtcatga    5820
taataatggt ttcttagacg tcaggtggca cttttcgggg aaatgtgcgc ggaaccccta    5880
tttgtttatt tttctaaata cattcaaata tgtatccgct catgagacaa taaccctgat    5940
aaatgcttca ataatattga aaaggaaga gtatgagtat tcaacatttc cgtgtcgccc    6000
ttattccctt ttttgcggca ttttgccttc ctgtttttgc tcacccagaa acgctggtga    6060
aagtaaaaga tgctgaagat cagttgggtg cacgagtggg ttacatcgaa ctggatctca    6120
acagcggtaa gatccttgag agttttcgcc ccgaagaacg ttttccaatg atgagcactt    6180
ttaaagttct gctatgtggc gcggtattat cccgtattga cgccgggcaa gagcaactcg    6240
gtcgccgcat acactattct cagaatgact tggttgagta ctcaccggtc acagaaaagc    6300
atcttacgga tggcatgaca gtaagagaat tatgcagtgc tgccataacc atgagtgata    6360
acactgcggc caacttactt ctgacaacga tcggaggacc gaaggagcta accgcttttt    6420
tgcacaacat gggggatcat gtaactcgcc ttgatcgttg ggaaccggag ctgaatgaag    6480
ccataccaaa cgacgagcgt gacaccacga tgcctgtagc aatggcaaca acgttgcgca    6540
aactattaac tggcgaacta cttactctag cttcccggca acaattaata gactggatgg    6600
aggcggataa agttgcagga ccacttctgc gctcggccct tccggctggc tggtttattg    6660
ctgataaatc tggagccggt gagcgtgggt ctcgcggtat cattgcagca ctggggccag    6720
atggtaagcc ctcccgtatc gtagttatct acacgacggg gagtcaggca actatggatg    6780
aacgaaatag acagatcgct gagataggtg cctcactgat taagcattgg taactgtcag    6840
accaagttta ctcatatata ctttagattg atttaaaact tcattttaa tttaaaagga    6900 tctaggtgaa gatcctttt gataatctca tgaccaaaat cccttaacgt gagttttcgt    6960
tccactgagc gtcagacccc gtagaaaaga tcaaaggatc ttcttgagat cctttttttc    7020
```

```
tgcgcgtaat ctgctgcttg caaacaaaaa aaccaccgct accagcggtg gttttttttgc   7080 cggatcaaga gctaccaact cttttttccga aggtaactgg cttcagcaga gcgcagatac   7140
caaatactgt tcttctagtg tagccgtagt taggccacca cttcaagaac tctgtagcac    7200
cgcctacata cctcgctctg ctaatcctgt taccagtggc tgctgccagt ggcgataagt   7260
cgtgtcttac cgggttggac tcaagacgat agttaccgga taaggcgcag cggtcgggct   7320
gaacgggggg ttcgtgcaca cagcccagct tggagcgaac gacctacacc gaacctgaga   7380
tacctacagc gtgagctatg agaaagcgcc acgcttcccg aagggagaaa ggcggacagg   7440
tatccggtaa gcggcagggt cggaacagga gagcgcacga gggagcttcc agggggaaac   7500
gcctggtatc tttatagtcc tgtcgggttt cgccacctct gacttgagcg tcgatttttg   7560
tgatgctcgt caggggggcg gagcctatgg aaaaacgcca gcaacgcggc cttttttacgg   7620 ttcctggcct tttgctggcc ttttgctcac atgttctttc ctgcgttatc ccctgattct   7680
gtggataacc gtattaccgc ctttgagtga gctggcgggt ctagttaatg tgtaacgtaa   7740
cattagctag attttttttat tcaaaaaaat atttacaaat attaggaaat ttaagtgtaa   7800
aagagttgat aaatgattat attgggacta taatataatt aaggtcgatt gaattcgtta   7860
actaattaat caccaaaaag aatagagta tgaagtttgg aaatatttgt ttttcgtatc    7920
aaccaccagg tgaaactcat aagcaagtaa tggatcgctt tgttcggctt ggtatcgcct   7980
cagaagaggt agggtttgat acatattgga ccttagaaca tcattttaca gagtttggtc   8040
ttacgggaaa tttatttgtt gctgcggcta acctgttagg aagaactaaa acattaaatg   8100
ttggcactat gggggttgtt attccgacag cacacccagt tcgacagtta gaagacgttt   8160
tattattaga tcaaatgtcg aaaggtcgtt ttaattttgg aaccgttcga gggctatacc   8220
ataaagattt tcgagtattt ggtgttgata tggaagagtc tcgagcaatt actcaaaatt   8280
tctaccagat gataatggaa agcttacaga caggaaccat tagctctgat agtgattaca   8340
ttcaatttcc taaggttgat gtatatccca aagtgtactc aaaaaatgta ccaacctgta   8400
tgactgctga gtccgcaagt acgacagaat ggctagcaat acaagggcta ccaatggttc   8460
ttagttggat tattggtact aatgaaaaaa agcacagat ggaactctat aatgaaattg    8520
cgacagaata tggtcatgat atatctaaaa tagatcattg tatgacttat atttgttctg   8580
ttgatgatga tgcacaaaag gcgcaagatg tttgtcggga gtttctgaaa aattggtatg   8640
actcatatgt aaatgcgacc aatatctttta atgatagcaa tcaaactcgt ggttatgatt   8700
atcataaagg tcaatggcgt gattttgttt tacaaggaca tacaaacacc aatcgacgtg   8760
ttgattatag caatggtatt aaccccgtag gcactcctga gcagtgtatt gaaatcattc   8820
aacgtgatat tgatgcaacg ggtattacaa acattacatg cggatttgaa gctaatggaa   8880
ctgaagatga ataattgct tccatgcgac gctttatgac acaagtcgct cctttcttaa    8940
aagaacctaa ataaattact tatttgatac tagagataat aaggaacaag ttatgaaatt   9000
tggattattt tttctaaact ttcagaaaga tggaataaca tctgaagaaa cgttggataa   9060
tatggtaaag actgtcacgt taattgattc aactaaatat cattttaata ctgcctttgt   9120
taatgaacat cacttttcaa aaaatggtat tgttggagca cctattaccg cagctggttt   9180
tttattaggg ttaacaaata aattacatat tggttcatta aatcaagtaa ttaccaccca   9240
tcaccctgta cgtgtagcag aagaagccag tttattagat caaatgtcag agggacgctt   9300
cattcttggt tttagtgact gcgaaagtga tttcgaaatg gaattttta gacgtcatat    9360 ctcatcaagg caacaacaat ttgaagcatg ctatgaaata attaatgacg cattaactac   9420
```

-continued

```
aggttattgc catccccaaa acgactttta tgattttcca aaggtttcaa ttaatccaca    9480
ctgttacagt gagaatggac ctaagcaata tgtatccgct acatcaaaag aagtcgtcat    9540
gtgggcagcg aaaaaggcac tgcctttaac gtttaagtgg gaggataatt tagaaaccaa    9600
agaacgctat gcaattctat ataataaaac agcacaacaa tatggtattg atatttcgga    9660
tgttgatcat caattaactg taattgcgaa cttaaatgct gatagaagta cggctcaaga    9720
agaagtgaga gaatacttaa aagactatat cactgaaact taccctcaaa tggacagaga    9780
tgaaaaaatt aactgcatta ttgaagagaa tgcagttggg tctcatgatg actattatga    9840
atcgacaaaa ttagcagtgg aaaaaacagg gtctaaaaat attttattat cctttgaatc    9900
aatgtccgat attaaagatg taaaagatat tattgatatg ttgaaccaaa aaatcgaaat    9960
gaatttacca taataaaatt aaaggcaatt tctatattag attgccttttt tggcgcgcct   10020 attctaatgc ataataaata ctgataacat cttatatttt gtattatatt ttgtattatc   10080
gttgacatgt ataattttga tatcaaaaac tgattttccc tctattattt tcgagattta   10140
ttttcttaat tctctttaac aaactagaaa tattgtatat acaaaaaatt ataaataata   10200
gatgaatagt ttaattatag gtgttcatca atcgaaaaag caacgtatct tatttaaagt   10260
gcgttgcttt tttctcattt ataaggttaa ataattctca tatatcaagc aaagtgaca    10319
```

GROWTH-INDEPENDENT DETECTION OF CELLS

CROSS REFERENCE TO RELATED APPLICATIONS

This application is a continuation of International Application No. PCT/US2015/035611 filed Jun. 12, 2015, which claims the benefit of U.S. Provisional Application No. 62/011,660, filed on Jun. 13, 2014; the contents of which are incorporated by reference herein in their entireties, for all purposes.

SEQUENCE LISTING

The instant application contains a Sequence Listing which has been submitted electronically in ASCII format and is hereby incorporated by reference in its entirety. Said ASCII copy, created on Jun. 10, 2015, is named 29449PCT_CRF_sequencelisting.txt and is 25 kilobytes in size.

BACKGROUND

In the research laboratory, many studies employing cells are conducted using cultured cells that often exhibit logarithmic growth. In nature, however, cells are rarely in a logarithmic growth-rate and often are in a stationary state. This phenomenon is an important consideration in the development of clinical diagnostics for the detection of cells since clinical samples can contain cells that are not in a metabolic state that supports optimal growth. In some cases, cells can be obtained that do not grow under the assay conditions intended to detect the cells. As such, when testing for the presence of cells directly from a clinical or environmental sample, it can oftentimes be important to employ an assay that operates independent of cell growth.

Even when cells are isolated and cultured in the laboratory there can still be situations in which individual strains of isolated cells can exhibit varying growth characteristics. When such cells exhibit sub-optimal growth, this can lead to a cell not being detected by an assay that generally requires growth. Example 9 of WO 2014/145899 exemplifies this situation (See page 80, line 2-page 82, line 33, and FIG. 26B). In that assay, *S. aureus* cells were monitored for growth in the presence of clindamycin. The assay was intended for distinguishing a clindamycin susceptible vs. resistant phenotype making the determination based on the growth rate of the bacteria in the presence of clindamycin. In the assay, one clindamycin-resistant isolate of bacteria was misinterpreted as clindamycin-sensitive because the isolate exhibited a sub-optimal growth rate.

As such, assays that generally require a minimum amount of growth or a minimum growth rate may not detect target cells that do not exhibit the required growth characteristics during the assay.

Related patent applications include: PCT/US2014/026536, filed on Mar. 13, 2014, which is hereby incorporated by reference, in its entirety, for all purposes.

SUMMARY

Disclosed herein is a cellular detection method that operates independent of cell growth. While existing cellular detection methodologies benefit from cell growth, the methods disclosed herein demonstrate embodiments that are independent of cell growth.

The methods disclosed herein are generally independent of growth—which can be an important feature for detecting cells at a metabolic state that does not support adequate growth (e.g., cells encountered in clinical samples) and for strains of cells with lower than expected growth rates.

Disclosed herein are various methods, systems, and compositions for the growth independent detection of cells.

For example, a method disclosed herein can include a growth-independent method for detecting a microorganism of interest in a sample, comprising: contacting the sample with a plurality of non-replicative transduction particles (NRTPs) such that the plurality of NRTPs transduces one or more microorganisms of interest in the sample, wherein the plurality of NRTPs comprises a reporter nucleic acid sequence, and wherein the growth rate of the one or more microorganisms of interest is less than logarithmic phase; providing conditions for activation of the reporter nucleic acid sequence; and detecting a signal produced by the reporter nucleic acid sequence, wherein the presence of the signal indicates the presence of the one or more microorganisms of interest, and wherein the absence of the signal indicates the absence of the one or more microorganisms of interest.

As a further example, a composition disclosed herein can include a sample or a cell culture comprising a plurality of non-replicative transduction particles (NRTPs) and one or more microorganisms of interest, optionally wherein the plurality of NRTPs comprises a reporter nucleic acid sequence, and wherein the growth rate of the one or more microorganisms of interest is less than logarithmic phase.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Figures 1, 1A, 1B:
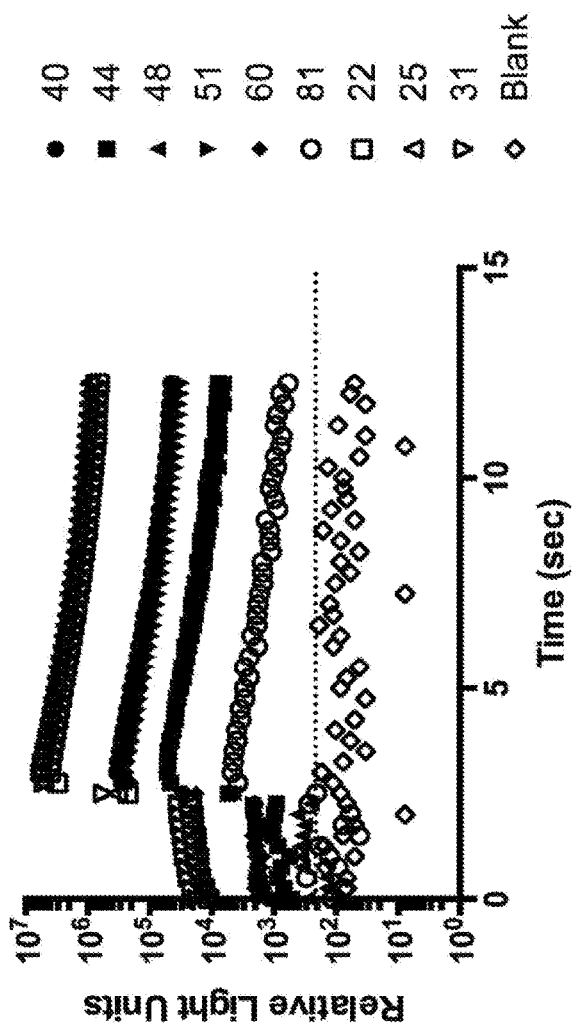
FIG. 1-FIG. 1A summarizes the ratio of colony forming units (CFUs) counts of MRSA at the end of the assay and at the beginning of the assay where most samples exhibited minimal growth during the 4-hour assay (e.g., 1-2 divisions) with two samples showing a decrease in growth (48 and 60), one sample showing no growth (51), and 3 samples exhibiting less than 0.4 divisions per hour (40, 51, and 81).
FIG. 1B shows that all samples tested produced a positive signal (relative light units. RLU) over background.

Terms used in the claims and specification are defined as set forth below unless otherwise specified.

As used herein, "reporter nucleic acid molecule" or "reporter nucleic acid sequence" refers to a nucleotide sequence comprising a DNA or RNA molecule capable of producing a signal. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

A "detectable indication of viability" refers to an indicator associated with a cell that can be observed and that demonstrates whether the cell is more or less viable or if its viability is affected, e.g., relative to a control cell, where the control cell can be the same cell at a different time point or a separate cell. Examples include one or more signals, one or more reporters, one or more markers, growth or lack thereof, light (e.g., light emitted by a luciferase) or lack thereof, etc.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that surrounds the protein coat.

"MRSA" refers to Methicillin-resistant *Staphylococcus aureus*.

"MSSA" refers to Methicillin-sensitive *Staphylococcus aureus*.

The term "ameliorating" refers to any therapeutically beneficial result in the treatment of a disease state, e.g., a disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term stringent hybridization conditions refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part 1, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT. FASTA, and TFASTA in the Wisconsin Genetics Software Package, Genetics Computer Group, 575 Science Dr., Madison. Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Lysogenic and Lytic Cycle of Viruses

Viruses undergo lysogenic and lytic cycles in a host cell. If the lysogenic cycle is adopted, the phage chromosome can be integrated into the bacterial chromosome, or it can establish itself as a stable plasmid in the host, where it can remain. If the lytic cycle of a lysogen is induced, the phage genome is excised from the bacterial chromosome and initiates the lytic cycle, which culminates in lysis of the cell and the release of phage particles. The lytic cycle leads to the production of new phage particles which are released by lysis of the host.

Certain temperate phage can exhibit lytic activity, and the propensity for this may vary with varying host bacteria. To illustrate this phenomenon, the lytic activity of two temperate S. aureus phages on ten MRSA clinical isolates was examined via plaque assay (Table 1). The phage φ11 exhibited lytic activity on 10 out of 10 clinical MRSA isolates and φ80α exhibited lytic activity on six of the 10 clinical MRSA isolates. Thus, reporter assays relying on the natural lysogenic cycle of phages can be expected to exhibit lytic activity sporadically.

TABLE 1

Lytic activity (denoted by the letter "x") of the S. aureus temperate phages φ11 and φ80α on ten clinical MRSA isolates

| MRSA isolate | φ11 | φ80α |
| --- | --- | --- |
| 1 | x | |
| 2 | x | |
| 3 | x | x |
| 4 | x | x |
| 5 | x | x |
| 6 | x | |
| 7 | x | x |
| 8 | x | |
| 9 | x | x |
| 10 | x | x |

In addition, virus-based reporter assays, such as phage-based reporters, can suffer from limited reactivity (i.e., analytical inclusivity) due to limits in the phage host range caused by host-based and prophage-derived phage resistance mechanisms. These resistance mechanisms target native phage nucleic acid that can result in the degradation or otherwise inhibition of the phage DNA and functions. Such resistance mechanisms include restriction systems that cleave phage DNA and CRISPR systems that target phage-derived sequences.

Both lytic activity and phage resistance can be inhibitory to assays based on reporter phages. Lytic activity can inhibit signal by destroying or otherwise inhibiting the cell in its ability to generate a detectable signal and thus affecting limits of detection by reducing the amount of detectable signal or preventing the generation of a detectable signal. Phage resistance mechanisms can limit the host range of the phage and limit the inclusivity of the phage-based reporter, similarly affecting limits of detection by reducing the amount of detectable signal or preventing the generation of a detectable signal. Both lytic activity and phage resistance caused by the incorporation of phage DNA in a reporter phage can lead to false-negative results in assays that incorporate these phage reporters.

Non-Replicative Transduction Particles (NRTPs), Methods for Producing Non-Replicative Transduction Particles (NRTP), and Related Assays A "transduction particle" refers to a virus capable of delivering a non-viral nucleic acid molecule into a cell. The virus can be a bacteriophage, adenovirus, etc.

A "non-replicative transduction particle" refers to a virus capable of delivering a non-viral nucleic acid molecule into a cell, but does not package its own replicated viral genome into the transduction particle. The virus can be a bacteriophage, adenovirus, etc.

Various NRTPs, methods of making the various NRTPs, and methods of using the NRTPs are described in: PCT/US2014/026536, filed on Mar. 13, 2014, which is hereby incorporated by reference, in its entirety, for all purposes. Examples of such methods of producing NRTPs include disruption/complementation systems employing lysogenized virus in which a sequence of DNA that is recognized by the viral packaging machinery is disrupted (e.g., via mutation, deletion, insertion, etc.), and the disruption is complemented by a reporter plasmid. In these systems, when the lytic cycle of the lysogenized virus is induced, the system produces virus particles but the particles carry plasmid DNA instead of virus DNA.

In some aspects, methods for the use of NRTPs as reporter molecules for use with endogenous or native inducers that target gene promoters within viable cells. In some embodiments, the method comprises employing a NRTP as a reporter, wherein the NRTP comprises a reporter gene that is operably linked to a promoter that controls the expression of a target gene within a target cell. When the NRTP that includes the reporter gene is introduced into the target cell, expression of the reporter gene is possible, e.g., via induction of the target gene promoter in the reporter nucleic acid molecule. In certain aspects, a reporter nucleic acid sequence is operatively linked to a constitutive promoter. In some aspects the constitutive promoter is a S. aureus clpB promoter.

In some embodiments, constructs (including NRTPs) comprise a reporter nucleic acid sequence that can include a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, a reporter nucleic acid sequence encodes a marker such as a detectable or selectable marker. The terms "marker" or "markers" encompass, without limitation, lipids, lipoproteins, proteins, cytokines, chemokines, growth factors, peptides, nucleic acids, genes, and oligonucleotides, together with their related complexes, metabolites, mutations, variants, polymorphisms, modifications, fragments, subunits, degradation products, elements, and other analytes or sample-derived measures. A marker can also include mutated proteins, mutated nucleic acids, variations in copy numbers, and/or transcript variants.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (luxA, luxB, luxAB, luc, rue, nluc, etc.). Reporter molecules can include a bacterial luciferase, a eukaryotic luciferase, an enzyme suitable for colorimetric detection (lacZ, HRP), a protein suitable for immunodetection, such as affinity peptides (His-tag. 3X-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Delivery of cell reporter nucleic acid sequences can be accomplished by various means including electroporation, chemical, biolistic, and glass bead transformation, transduction, transfection, vectors, conjugation, including, but not limited to, delivery via nucleic acid delivery vehicles including bacteriophage, virus, spheroplast, liposomes, virus-like particles, lipid-DNA complexes, lipoplexes, polymer-DNA complexes, polyplexes, etc.

In some aspects, the methods, systems, and compositions disclosed herein comprise a sample in contact with a fatty aldehyde bacterial luciferase substrate reagent to, e.g., produce a signal. Examples of fatty aldehyde bacterial luciferase substrate reagents can include tridecanal as well as other similar fatty aldehyde bacterial luciferase substrate reagents known in the art. Fatty aldehydes of various carbon chain lengths are suitable including hexanal, heptanal, octanal, nonanal, decanal, udecanal, dodecanal, and/or tetradecanal.

In some aspects a reporter nucleic acid sequence can produce a signal. In certain aspects a signal is a luminescence signal. In some aspects a signal can be measured in relative light units (RLU) emitted by the signal Various devices are known in the art detecting a signal from a reporter nucleic acid sequence. Devices for detecting light emission include photomultiplier tubes, photo diodes, and/or avalanche photo diodes. Detection can be accomplished by simply collecting light signal from an area or volume and/or by imaging an area or volume.

In some aspects a signal is greater than a background threshold, e.g., where the background threshold is calculated from an average background signal plus 0×, 1×, 2×, or 3× the standard deviation of the average background signal.

In some aspects a signal can be detected at a limit of detection (LoD) of less than or equal to 10000-1, 1000-10, 1000-100, 100-1, 10,000, 1,000, 500, 400, 300, 200, 100, 90, 80, 70, 60, 50, 40, 30, 20, 10, 9, 8, 7, 6, 5, 4, or 3 colony forming units (CFU). In some aspects, a signal can be detected at a LoD of less than or equal to five CFU, or a signal can be detected at a LoD of less than or equal to three CFU, or a signal can be detected at a LoD of less than or equal to two CPU, or a signal can be detected at a LoD of less than or equal to one CFU.

In certain aspects, the sensitivity or specificity of a method of using a given NRTP to detect a cell can be determined, e.g., as described in PCT/US2014/026536, filed on Mar. 13, 2014.

In some aspects, a method produces at least 80-100, 80-90, 90-100, 85-95, 90-95, 80, 81, 82, 83, 84, 85, 86, 87, 88, 89, 90, 91, 92, 93, 94, 95, 96, 97, 98, 99, or 100% specificity of detection with reference to a standard cell culture-based assay.

In some aspects, a method produces at least 80-100, 80-90, 90-100, 85-95, 90-95, 80, 81, 82, 83, 84, 85, 86, 87, 88, 89, 90, 91, 92, 93, 94, 95, 96, 97, 98, 99, or 100% sensitivity of detection with reference to a standard cell culture-based assay.

In some aspects, a method achieves at least 80-100, 80-90, 90-100, 85-95, 90-95, 80, 81, 82, 83, 84, 85, 86, 87, 88, 89, 90, 91, 92, 93, 94, 95, 96, 97, 98, 99, or 100% specificity of detection and at least 80-100, 80-90, 90-100, 85-95, 90-95, 80, 81, 82, 83, 84, 85, 86, 87, 88, 89, 90, 91, 92, 93, 94, 95, 96, 97, 98, 99, or 100% sensitivity of detection with reference to a standard cell culture-based assay.

Cells and Samples

Cells disclosed herein can include prokaryotes and eukaryotes. In some aspects, a cell can be a microorganism. The term "microorganism" means prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism. A microorganism can include a Methicillin Resistant *Staphylococcus aureus* (MRSA) cell, *Staphylococcus aureus*, *Staphylococcus* spp., Enterobacteriaceae, *Enterococcus* spp. *Streptococcus* spp., *Acinetobacter* spp., *Pseudomonas* spp., *Stenotrophomonas* spp., or *Mycobacterium* spp.

The term "sample" can include a single cell or multiple cells or an aliquot of body fluid, taken from an environment or subject, by means including venipuncture, excretion, ejaculation, massage, biopsy, needle aspirate, lavage sample, scraping, surgical incision, swabbing, or intervention or other means known in the art. In some aspects, a sample can include a clinical sample such as a sample obtained from a subject in a clinical setting such as a hospital. In some aspects, a sample is a nasal swab sample, a rectal swab sample, a blood sample, a positive blood culture sample, a skin/soft tissue sample, a bronchoalveolar lavage sample, a sputum sample, a stool sample, a urine sample, and/or a sample of an isolated microorganism.

The term "subject" encompasses a cell, tissue, or organism, human or non-human, whether in vivo, ex vivo, or in vitro, male or female.

Antimicrobial Agents

An "antimicrobial agent" refers to a compound that can kill inhibit the growth, or otherwise compromise the viability of one or more microorganisms. Antimicrobial agents include antibiotics, antifungals, antiprotozoals, antivirals, and other compounds.

An antimicrobial agent can include cefoxitin, a β-lactam, an extended-spectrum β-lactam, an Aminoglycoside, an Ansamycin, a Carbacephem, Carbapenems, any generation of Cephalosporin, a Glycopeptide, a Lincosamide, a Lipopeptide, a Macrolide, a Monobactam, a Nitrofuran, an Oxazolidonone, a Penicillin, a Polypeptide, a Quinolone, a Fluoroquinolone, a Streptogramin, a Sulfonamide, a Tetracycline, a Rifampicin, a mycobacterial antibiotic, Chloramphenicol, and Mupirocin.

In some aspects, the methods, systems, and compositions disclosed herein can include an antimicrobial agent in contact with a sample and detection of a signal produced by a reporter nucleic acid sequence of an NRTP to determine whether one or more microorganisms of interest is susceptible or non-susceptible to the antimicrobial agent. In certain aspects, the antimicrobial agent is an antibiotic.

In some aspects, the methods, systems, and compositions disclosed herein can include varying pre-determined concentrations of antimicrobial agent in contact with a sample and detecting the amount of a signal to determine the minimum inhibitory concentration of the one or more microorganisms of interest to the antimicrobial agent. In certain aspects, the antimicrobial agent is an antibiotic.

Cell Growth

Methods, systems, and compositions disclosed herein are typically growth independent methods, systems, and compositions, e.g., for the detection of one or more cells in a sample derived from a subject. For example, methods described herein can include isolating or obtaining a sample from a subject of interest and directly contacting an NRTP described herein with the sample (or a culture comprising the sample) for detecting a cell or set of cells of interest that may or may not be present in the sample, regardless of growth.

Various methods for determining growth are known in the art, e.g., methods that detect bulk growth of cells, e.g., by measuring an increasing in optical density of a sample and/or methods that measure growth of discrete cells in a sample such as microscopy, automated microscopy, and/or traditional culture of organisms on solid media to detect the presence of a colony of bacteria on the solid media.

Various culture conditions can be used for detecting a cell in a growth-independent manner, e.g., one or mere nutrient formulations that support a cell's ability to transcribe and translate regardless of cell replication rate. In some aspects, culture conditions include limited nutrient conditions, e.g., such as those provided by Roswell Park Memorial Institute (RPMI) media (Fisher Scientific Company, LLC). In some aspects, culture conditions are selected such that they mimic the metabolic state of cells in a natural environment. In some aspects, culture conditions are limited to or include use of a sample that is in a state similar to or identical to its state in its natural environment.

In some aspects, the growth rate of a microorganism or population of microorganisms is less than logarithmic phase. In some aspects, the growth rate of a microorganism or population of microorganisms can be less than or equal to 0.05, 0.1, 0.2, 0.3, 0.4, 0.5, 1, 2, or 3 divisions per hour. In some aspects, the growth rate of a microorganism or population of microorganisms can be less than or equal to 1 cell division per 4 hour period, less than or equal to 2 cell divisions per 4 hour period, less than or equal to 3 cell divisions per 4 hour period, less than or equal to 4 cell divisions pet 4 hour period, less than or equal to 5 cell divisions per 4 hour period, less than or equal to 6 cell divisions per 4 hour period, less than or equal to 7 cell divisions per 4 hour period, less than or equal to 8 cell divisions per 4 hour period, less than or equal to 9 cell divisions per 4 hour period, or less than or equal to 10 cell divisions per 4 hour period. In some aspects, the growth rate of a microorganism or population of microorganisms can be less than or equal to 0.1 divisions per hour, in particular when the microorganism or population of microorganisms is or includes Methicillin Resistant *Staphylococcus aureus* (MRSA).

In some aspects, the growth of a microorganism or population of microorganisms can be characterized as stationary phase, less than stationary phase, or greater than stationary phase but less than log phase. In some aspects, a microorganism or population of microorganisms can be undergoing no growth or no detectable growth. In some aspects, the growth of a microorganism or population of microorganisms can negative (e.g., greater cell death is occurring than cell division) or homeostatic (e.g., cell death and division are relatively equal).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature, See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992).

Example 1

Deletion/Complementation Packaging System

The following is an example of the design and construction of a deletion/complementation-based packaging system for producing non-replicative transduction particles.

The materials used for developing the packaging system are listed below:

Bacterial Strains:

RN4220 is a restriction defective *S. aureus* strain that is a non-lysogenic derivative of NCTC 8325 and is an efficient recipient for *E. coli* DNA. It was first described in Kreiswirth, B. N. et al., *The toxic shock syndrome exotoxin structural gene is not detectably transmitted by a prophage.* Nature, 1983. 305(5936): p. 709-712.

RN10616 is derived by lysogenizing RN4220 with bacteriophage φ80α. Ubeda, C. et al., *Specificity of staphylococcal phage and SaPI DNA packaging as revealed by integrase and terminase mutations.* Molecular Microbiology, 2009. 72(1): p. 98-108.

ST24 is derived from deleting the small terminase gene terS from the lysogenized bacteriophage φ80α in RN10616. Ubeda, C. et al., *Specificity of staphylococcal phage and SaPI DNA packaging as revealed by integrase and terminate mutations.* Molecular Microbiology, 2009. 72(1): p. 98-108.

Vectors:

Examples of plasmids that can be used as source plasmids for cassettes, in some embodiments of the invention are described in Charpentier, E., et al., *Novel Cassette-Based Shuttle Vector System for Gram-Positive Bacteria.* Appl. Environ. Microbiol., 2004. 70(10): p. 6076-6085.

The following GenBank accession numbers can be used for cassette sequences:

SEQ ID NO:1 (*S. aureus* pT81 plasmid origin or replication copy number variant pT181cop-623 repC)
M21136 (tetA(M))
SEQ ID NO:2 ($P_{clpB}$ promoter sequence)
SEQ ID NO:3 (φ11 small terminase (terS) gene sequence)
L09137 (amp ColE1 ori)
X06758 (luxAB)
M62650 (Transcription Termination)

terS Deletion: The construction of the terS knockout strain ST24 can be accomplished via an allelic-exchange-based strategy resulting in an in-frame deletion removing most of the coding sequence of the φ80α small terminase gene. The details of this strategy are described in Ubeda, C. et al., *Specificity of staphylococcal phage and SaPI DNA packaging a revealed by integrase and terminase mutations.* Molecular Microbiology, 2009. 72(1): p. 98-108.

An exemplary sequence of a terS knockout strain is shown in SEQ ID NO:4, (shown in the sequence listing below). SEQ ID NO:4 is a RN10616 genomic sequence loci showing the φ80α terS deletion and complementation.

Vector Construction: The GW80A0001 vector is an *E. coli/S. aureus* shuttle vector. The vector contains *S. aureus* (pT181cop-623 repC) and *E. coli* (ColE1ori) origins of replication, the selectable markers for ampicillin (amp) and tetracycline (tet(M)) resistance for selection in *E. coli* and *S. aureus*, respectively, the φ11 small terminase (terS) gene sequence that includes its own promoter, the luxA and luxB genes are from *Vibrio harveyi* operatively linked to the constitutive *S. aureus* $P_{clpB}$ promoter, and a transcription termination sequence (TT).

The resulting vector (pGW80A0001, SEQ ID NO:5) can be constructed in a variety of manners that are known to one of skill in the an. In one example, the tet(M) cassette and luxAB genes can be obtained via PCR amplification from the publically available pCN36 and pCN58 vectors (Charpentier, E., et al.). $P_{clpB}$ can be obtained from PCR amplification from *S. aureus* RN4220 and terS can be obtained via PCR amplification from RN10616. A vector backbone can be obtained by removing the ermC gene from the publically available vector pCN48 (Charpentier, E., et al.), and the various components of the final vector pGW80A001 can be assembled onto this vector backbone via appropriately designed restriction enzyme-based cloning.

Deletion/Complementation Packaging System: The packaging system can include the terS knockout strain ST24 complemented with the vector pGW80A0001 to generate strain GW24. As known to one of skill in the art, the manner of constructing this system can be accomplished by transformation ST24 with vector pGW80A0001. The vector pGW80A0001 can be maintained in cultures of the transformed ST24 by growing the transformant in the presence of 5 ug/mL of tetracycline.

Production of Transduction Particles Carrying Plasmid DNA: Non-replicative transduction particles carrying vector pGW80A0001 can be produced from GW24 via a Mitomycin C-induction method that was first demonstrated in *E. coli* and is now a standard technique for obtaining prophages from lysogenized bacteria. Otsuji, N. et al., *Induction of Phage Formation in the Lysogenic Escherichia coli K-12 by Mitomycin C* Nature, 1959. 184(4692): p. 1079-1080. This prophage induction method results in induction of the φ80α lytic cycle in which the prophage excises from the GW24 genome, produces phage structural elements, and packages pGW80A0001 concatameric DNA in progeny phage particles. The resulting cell lysate is then collected and contains non-replicative transduction particles, each consisting of bacteriophage φ80α particles carrying a linear concatamer of pGW80A0001 DNA.

Example 2

Non-Replicative Transduction Particle-Based Reporter System

The non-replicative transduction particles described above can be used in a reporter system for detecting the presence of viable bacteria via the expression of a reporter molecule (e.g. luxAB). When this transduction particle introduces a reporter vector (e.g. pGW80A0001) into a cell within the host range of the transduction particle, cells in which the promoter (e.g. $P_{clpB}$) is recognized by the cells transcription machinery are able to drive the expression of the reporter molecule within that cell.

To test the functionality of non-replicative transduction particles as reporters for detecting the presence of *S. aureus* cells, various MSSA/MRSA reporter assays were developed. In an embodiment, a non-replicative transduction particle was developed from a *S. aureus*-specific bacteriophage, and the bacterial luciferase genes luxAB under the control of a constitutive promoter were incorporated. When the non-replicative transduction particle delivered the reporter nucleic acid into *S. aureus*, the constitutive promoter expressed luxAB suitable for reporting on the presence of a viable *S. aureus*.

In addition, the antibiotic cefoxitin was added prior to, simultaneously with, or after the addition of the transduction particles to a sample containing *S. aureus* cells. If the cells were not phenotypically resistant to cefoxitin (i.e., were not MRSA), luminescence was decreased or eliminated, indicating that the cells were MSSA. If, however, the cells were phenotypically resistant to cefoxitin (i.e., were MRSA), increased or detectable luminescence was observed, indicating that the cells were MRSA.

Example 3

Growth-Independent Detection of Cells

As an example, a test was conducted to evaluate the impact of cell replication on the ability to detect a target cell. A *S. aureus* transduction particle and assay as described in Example 1 (see also PCT/US2014/026536, Example 2) was employed in an assay for detecting MRSA. The transduction particle causes viable *S. aureus* cells to produce bacterial luciferase that is capable of mediating a luminescence reaction that is monitored using a photomultiplier tube that measures relative light units (RLU) emitted by the luminescence reaction. When testing for MRSA, the assay employs cefoxitin such that MSSA does not produce a luminescence signal while MRSA does produce a luminescence signal in the assay. Briefly, cultures of clinical isolates of MRSA obtained from the Network for Antimicrobial Resistance in *Staphylococcus aureus* (NARSA) were prepared under limited nutrient conditions of culturing in Roswell Park Memorial Institute (RPMI) media (Fisher Scientific Company, LLC) in order to produce cell cultures with cells exhibiting limited metabolic activity—i.e. mimicking the metabolic state of cells in a natural environment. Cell cultures were normalized to an OD600=0.1 and used to inoculate samples. Samples were mixed with transduction particle reagent described in Example 2 (see also PCT/US2014/026536, Example 7) and cefoxitin and incubated for 4 Fr at 37° C. then tested for the production of luminescence after the addition of a fatty aldehyde bacterial luciferase substrate reagent (tridecanal). In addition to running the luminescence assay, the amount of bacteria in each sample was quantified before the addition of transduction particles/incubation and after incubation/before the addition of substrate by plating an aliquot of each sample of TSB agar and enumerating the number of resulting colonies after 18-24 hours of incubation with each sample enumerated as total CFU in the sample at each time point.

FIG. 1 summarizes the data obtained from the test. FIG. 1*a* summarizes the ratio of CFU after (t=4 h) and before (t=0 h) the assay. FIG. 1*b* summarizes the signal produced from the samples summarized in FIG. 1*a*, where the dotted line at ~200 RLU is the background threshold calculated from the average background signal plus 3 times its standard deviation.

The results indicate that the assay did not require bacterial growth to detect the target cells. The analysis of bacterial growth during the assay revealed little to no growth during the assay despite a continuous increase of signal product in MRSA. As shown, FIG. 1*a* summarizes the ratio of CFU counts of MRSA at the end of the assay and at the beginning of the assay where most samples exhibited minimal growth during the 4-hour assay (e.g., 1-2 divisions) with two samples showing a decrease in growth (48 and 60), one sample showing no growth (51), and 3 samples exhibiting less than 0.4 divisions per hour (40, 51, and 81). As illustrated in FIG. 1*b*, all samples produced a positive signal during the assay. Despite exhibiting little to no growth, all samples tested produced a positive signal (RLU) over background.

Example 4

Growth-Independent Detection of Cells from Clinical Samples

As an example, a test was conducted to evaluate the impact of cell replication on the ability to detect a target cell directly from clinical samples.

A *S. aureus* transduction particle and assay as described in Example 1 (see also PCT/US2014/026536, Example 2) was employed in an assay for detecting MRSA. The transduction particle causes viable *S. aureus* cells to produce bacterial luciferase that is capable of mediating a luminescence reaction that is monitored using a photomultiplier tube that measures relative light units (RLU) emitted by the luminescence reaction. When testing for MRSA, the assay employs cefoxitin such that MSSA does not produce a luminescence signal while MRSA does produce a luminescence signal in the assay. Briefly, remnant nasal swab samples collected from patients by a hospital institution for the purpose of MRSA surveillance were tested for the presence of MRSA using the transduction particle assay. Samples were mixed with transduction particle reagent as described in Example 2 (see also PCT/US2014/026536, Example 7) and cefoxitin and incubated for 4 hr at 37° C. then tested for the production of luminescence after the addition of a fatty aldehyde bacterial luciferase substrate reagent (tridecanal). In addition to running the luminescence assay, the amount of bacteria in each sample was quantified before the addition of transduction particles/incubation and after incubation/before addition of substrate by plating an aliquot of each sample of TSB agar and enumerating the number of resulting colonies after 18-24 hours of incubation with each sample enumerated as total CFU in the sample at each time point.

Figures 2, 2A, 2B:
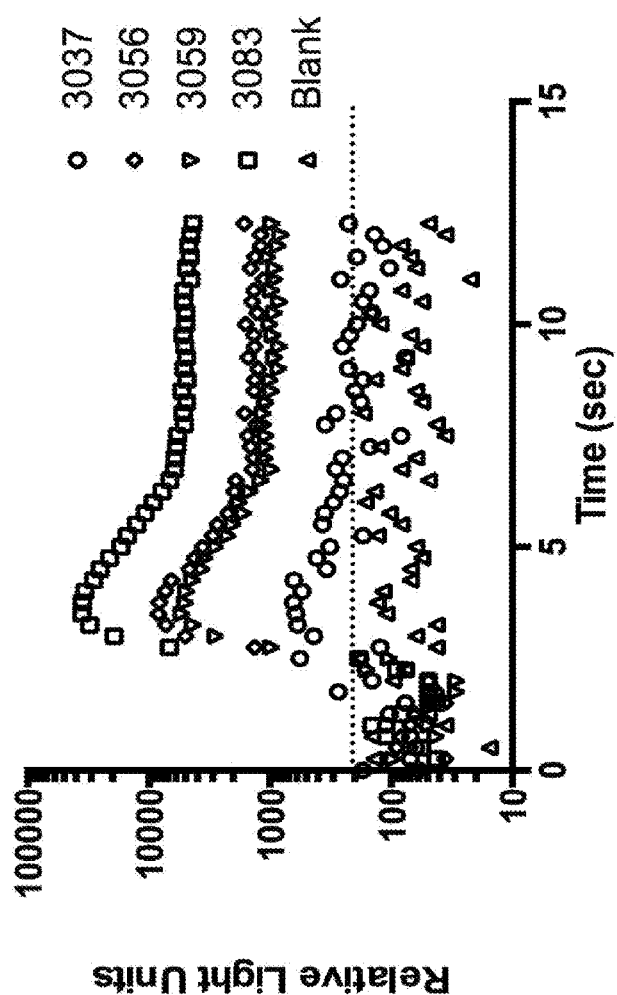
FIG. 2-FIG. 2A summarizes the ratio of CFU counts of MRSA at the end of the assay and at the beginning of the assay where most samples exhibited minimal growth during the 4-hour assay (e.g., 1-2 divisions) and one sample (3037) showed a decrease in growth.
FIG. 2B shows that all samples produced a positive signal (RLU) during the assay over background.

FIG. 2 summarizes the data obtained from four clinical samples that were positive for MRSA. FIG. 2*a* summarizes the ratio of CFU after (t=4 h) and before (t=0 h) the assay. FIG. 2*b* summarizes the signal produced from the four clinical samples summarized in FIG. 2*a*, where the dotted line at ~200 RLU is the background threshold calculated from the average background signal plus 3 times its standard deviation.

The results indicate that the assay did not require bacterial growth to detect the target cells. The analysis of bacterial growth during the assay revealed little to no growth during the assay despite a continuous increase of signal product in MRSA. As shown, FIG. 2*a* summarizes the ratio of CFU counts of MRSA at the end of the assay and at the beginning of the assay where most samples exhibited minimal growth during the 4-hour assay (e.g., 1-2 divisions) and one sample (3037) showed a decrease in growth. As illustrated in FIG. 2*b*, all samples produced a positive signal during the assay. Despite exhibiting little to no growth, all samples tested produced a positive signal (RLU) over background.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

---

SEQUENCES

SEQ ID NO: 1
S. aureus pT181 plasmid origin or relication copy number variant pT181cop-623 repC

```
TTTGCGGAAAGAGTTAGTAAGTTAACAGAAGACGAGCCAAACCTAAATGG
TTTAGCAGGAAACTTAGATAAAAAAATGAATCCAGAATTATATTCAGAAC
AGGAACAGCAACAAGAGCAACAAAAGAATCAAAAACGAGATAGAGGTATG
CACTTATAGAACATGCATTTATGCCGAGAAAACTTATTGGTTGGAATGGG
CTATGTGTTAGCTAACTTGTTAGCGAGTTGGTTGGACTTGAATTGGGATT
AATCCCAAGAAAGTACCGGCTCAACAACCCATAAAGCCCTGTAGGTTCCG
NCCAATAAGGAAATTGGAATAAAGCAATAAAAGGAGTTGAAGAAATGAAA
TTCAGAGAAGCCTTTGAGAATTTTATAACAAGTAAGTATGTACTTGGTGT
TTTAGTAGTCTTAACTGTTTACCAGATAATACAAATGCTTAAATAAAAAA
AGACTTTGATCTGATTAGACCAAATCTTTTGATAGTGTTTATATTAATAACA
AAATAAAAAGGAGTCGCTCACGCCCTACCAAAGTTTGTGAACGACATCAT
TCAAAGAAAAAAACACTGAGTTGTTTTTATAATCTTGTATATTTAGATAT
TAAACGATATTTAAATATACATCAAGATATATATTTGGGTGAGCGATTAC
TTAAACGAAATTGAGATTAAGGAGTCGATTTTTTATGTATAAAAACAATC
ATGCAAATCATTCAAATCATTTGGAAAATCACGATTTAGACAATTTTTCT
AAAACCGGCTACTCTAATAGCCGGTTGGACGCACATACTGTGTGCATATC
TGATCCAAAATTAAGTTTTGATGCAATGACGATCGTTGGAAATCTCAACC
GAGACAACGCTCAGGCCCTTTCTAAATTTATGAGTGTAGAGCCCCAAATA
AGACTTTGGGATATTCTTCAAACAAAGTTTAAAGCTAAAGCACTTCAAGA
AAAAGTTTATATTGAATATGACAAAGTGAAAGCAGATAGTTGGGATAGAC
GTAATATGCGTATTGAATTTAATCCAAACAAACTTACACGAGATGAAATG
ATTTGGTTAAACAAAATATAATAAGCTACATGGAAGATGACGGTTTTAC
AAGATTAGATTTAGCCTTTGATTTTGAAGATGATTTGAGTGACTACTATG
CAATGTCTGATAAAGCAGTTAAGAAAACTATTTTTTATGGTCGTAATGGT
AAGCCAGAAACAAAATATTTTGGCGTGAGAGATAGTAATAGATTTATTAG
AATTTATAATAAAAAGCAAGAACGTAAAGATAATGACGATGCTGAAGTTA
TGTCTGAACATTTATGGCGTGTAGAAATCGAACTTAAAAGAGATATGGTG
GATTACTGGAATGATTGCTTTAGTGATTTACATATCTTGCAACCAGATTG
GAAAACTATCCAACGCACTGCGGATAGAGCAATAGTTTTATGTTATTGA
GTGATGAAGAAGAATGGGGAAAGCTTCACAGAAATTCTAGAACAAAATAT
AAGAATTTGATAAAAGAAATTTCGCCAGTCGATTTAACGGACTTAATGAA
ATCGACTTTAAAAGCGAACGAAAAACAATTGCAAAAACAAATCGATTTTT
GGCAACATGAATTTAAATTTTGGAAATAGTGTACATATTAATATTACTGA
ACAAAAATGATATATTTAAACTATTCTAATTTAGGAGGATTTTTTTATGA
AGTGTCTATTTAAAAATTTGGGGAATTTATATGAGGTGAAAGAATAATTT
ACCCCTATAAACTTTAGCCACCTCAAGTAAAGAGGTAAAATTGTTTAGTT
TATATAAAAAATTTAAAGGTTTGTTTTATAGCGTTTTATTTTGGCTTTGT
ATTCTTTCATTTTTTAGTGTATTAAATGAAATGGTTTTAAATGTTTCTTT
ACCTGATATTGCAAATCATTTTAATACTACTCCTGGAATTACAAACTGGG
TAAACACTGCATATATGTTAACTTTTTCGATAGGAACAGCAGTATATGGA
AAATTATCTGATTATATAAATATAAAAAATTGTTAATTATTGGTATTAG
TTTGAGCTGTCTTGGTTCATTGATTGCTTTTATTGGGCCCACCTAGGCAA
ATATGCTCTTACGTGCTATTATTTAAGTGACTATTTAAAAGGAGTTAATA
AATATGCGGCAAGGTATTCTTAAATAAACTGTCAATTTGATAGCGGGAAC
AAATAATTAGATGTCCTTTTTAGGAGGGCTTAGTTTTTTGTACCCAGTT
TAAGAATACCTTTATCATGTGATTCTAAAGTATCCAGAGAATATCTGTAT
GCTTTGTATACCTATGGTTATGCATAAAAATCCCAGTGATAAAGATTTT
ATCACTGGGATTTTTATGCCCTTTTGGGTTTTTGAATGGAGGAAAATCAC
ATGAAAATTATTAATATTGGAGTTTTAGCTCATGTTGATGCAGGAAAAAC
TACCTTAACAGAAAGCTTATTATATAACAGTGGAGCGATTACAGAATTAG
GAAGCGTGGACAAAGGTACAACGAGGACGGATAATACGCTTTTAGAACGT
CAGAGAGGAATTACAATTCAGACAGGAATAACCTCTTTTCAGTGGGAAAA
TACGAAGGTGAACATCATAGACACGCCAGGACATATGGATTTCTTAGCAG
AAGTATATCGTTCATTATCAGTTTTAGATGGGGCAATTCTACTGATTTCT
GCAAAAGATGGCGTACAAGCACAAACTCGTATATTATTTCATGCACTTAG
GAAAATGGGGATTCCCACAATCTTTTTTATCAATAAGATTGACCAAAATG
GAATTGATTTATCAACGGTTTATCAGGATATTAAAGAGAAACTTTCTGCC
GAAATTGTAATCAAACAGAAGGTAGAACTGTATCCTAATATGTGTGTGAC
GAACTTTACCGAATCTGAACAATGGACATACGGTAATAGAGGGAAACGTA
ACCTTTTAGAGAAATATATGTCCGGTAAATCATTAGAAGCATTGGAACTC
GAACAAGAGGAAAGCATAAGATTTCAGAATTGTTCTCTGTTCCCTCTTTA
TCATGGAAGTGCAAAAAGTAATATAGGGATTGATAACCTTATAGAAGTTA
TTACTAATAAATTTTATTCATCAACACATCGAGGTCCGTCTGAACTTTGC
GGAAATGTTTTCAAAATTGAATATACAAAAAAAGACAACGTCTTGCATA
TATACGCCTTTATAGTGGAGTACTACATTTACGAGATTCGGTTAGAGTAT
CAGAAAAAGAAAAAATAAAAGTTACAGAAATGTATACTTCAATAAATGGT
GAATTATGTAAGATTGATAGAGCTTATTCTGGAGAAATTGTTATTTTGCA
AAATGAGTTTTTGAAGTTAAATAGTGTTCTTGGAGATACAAAACTATTGC
CACAGAGAAAAAGATTGAAAATCCGCACCCTCTACTACAAACAACTGTT
GAACCGAGTAAACCTGAACAGAGAGAAATGTTGCTTGATGCCCTTTTGGA
AATCTCAGATAGTGATCCGCTTCTACGATATTACGTGGATTCTACGACAC
ATGAAATTATACTTTCTTTCTTAGGGAAAGTACAAATGGAAGTGATTAGT
GGACTGTTGCAAGAAAAGTATCATGTGGAGATAGAACTAAAAGAGCCTAC
AGTCATTTATATGGAGAGACCGTTAAAAAATGCAGAATATACCATTCACA
TCGAAGTGCCGCCAAATCCTTTCTGGGCTTCCATTGGTTTATCTGTATCA
CCGCTTCCGTTGGGAAGTGGAATGCAGTATGAGAGCTCGGTTTCTCTTGG
ATACTTAAATCAATCATTTCAAAATGCAGTTATGGAAGGGGTACGCTATG
GTTGCGAACAAGGATTATATGGTTGGAATGTGACGGATTGTAAAATCTGT
TTTAAGTACGGTTTATACTATAGCCCTGTTAGTACTCCAGCAGATTTTCG
GATGCTTACTCCTATTGTACTGGAGCAAGCCTTTAGAAAAGCTGGAACAG
AATTGTTAGAGCCATATCTTAGTTTTAAAGTTTATGCACCACAGGAATAT
CTTTCNCGGGCATATAACGATGCTCCCAAATATTGTGCAAATATCGTAAA
TACTCAACTGAAAAATAATGAGGTCATTATTATTGGAGAAATTCCTGCTC
GATGTATTCAAGATTATCGCAATGATTTAACTTTTTTTACAAATGGGCTT
AGTGTTTGTTTAGCAGAGCTAAAAGGATATCAGGTTACCACTGGCGAACC
TGTTTGCCAGACCCGTCGTCTAAATAGTCGGATAGATAAAGTAAGATATA
TGTTCAATAAAATAACTTAGTGCGTTTTATGTTGTTATATAAATATGGTT
TCTTATTAAATAAGATGAAATATTCTTTAATATAGATTTGAATTAAAGTG
GAAAGGAGGAGATTGTTATTATAAACTACAAGTGGATATTTGTGTCCTATT
TGTGGAAATAAAACAAGACTACGAATACGAGTGGATACTATACTTAAAAA
TTTCCCTTTATACAGCCCCAAATGTAAGAACGAAACTTTAATTAATGTTC
AAAAAATGAATATAATAACAATCAAAGAGCCAGACGCCAAGACGCAGAGC
CGATAATTTGAGAAATGAAACTCTCATCTTATCGGCTCTTTTTGTTTATC
TGAATTTTACTGACTAGCCTTCAATATTTCC
```

SEQ ID NO: 2
S. aureus P<sub>clbB</sub> Promoter Sequence

```
GTCTAGTTAATGTGTAACGTAACATTAGCTAGATTTTTTATTCAAAAAA
ATATTTACAAATATTAGGAAATTTAAGTGTAAAAGAGTTGATAAATGATT
ATATTGGGACTATAATATAATTAAGGTC
```

SEQ ID NO: 3
Sequence containing native terS gene

```
AATTGGCAGTAAAGTGGCAGTTTTTGATACCTAAAATGAAGATATTATGAT
AGTGTAGGATATTGACTATCTTACTGCGTTTCCCTTATCGCAATTAGGAA
TAAAGGATCTATGTGGGTTGGCTGATTATAGCCAATCCTTTTTTAATTTT
AAAAAGCGTATAGCGCGAGAGTTGGTGGTAAATGAAATGAACGAAAAACA
AAAGAGATTCGCAGATGAATATATAATGAATGGATGTAATGGTAAAAAAG
CAGCAATTTCGACAGGTTATAGTAAGAAAACAGCAGAGTCTTTAGCAAGT
CGATTGTTAAGAAATGTTAATGTTTCGGAATATATTAAAGAACGATTAGA
ACAGATACAAGAAGAGCGTTTAATGAGCATTACAGAAGCTTTAGCGTTAT
CTGCTTCTATTGCTAGAGGAGAACCTCAAGAGGCTTACAGTAAGAAATAT
GACCATTTAAACGATGAAGTGGAAAAAGAGGTTACTTACACAATCACACC
AACTTTTGAAGAGCGTCAGAGATCTATTGACCACATACTAAAAGTTCATG
GTGCGTATATCGACAAAAAAGAAATTACTCAGAAGAATATTGAGATTAAT
ATTGGTGAGTACGATGACGAAAGTTAAATTAAACTTTAACAAACCATCTA
ATGTTTCAACAG
```

SEQ ID NO: 4
RN10616 genomic sequence loci showing the tp80a terS deletion and complementation. terS=Bracketed Text, Deletion = Underlined, Complement = Bold

```
ATTAGACAACAAACAAGTCATTGAAAATTCCGACTTATTATTCAAAAAGA
AATTTGATAGCGCAGATATACAAGCTAGGTTAAAAGTAGGCGATAAGGTA
GAAGTTAAAACAATCGGTTATAGAATACACTTTTTAAATTTATATCCGGT
CTTATACGAAGTAAAGAAGGTAGATAAACAATGATTAAACAAATACTAAG
ACTATTATTCTTACTAGCAATGTATGAGTTAGGTAAGTATGTAACTGAGC
AAGTATATATTATGATGACGGCTAATGATGATGTAGAGGTGCCGAGTGAC
TTCGCGAAGTTGAGCGATCAGTCAGATTTGATGAGGGCGGAGGTGACGGA
GTAGATGATGTGGTTAGTCATAGCAATTATATTACTAGTCATCTTATTGT
TTGGTGTGATGTTGCAAGCTGAACAGTTAAAAGGCGATGTGAAAGTTAAA
GAGCGGGAGATAGAGATATTAAGAAGTAGATTGAGACATTTTGAAGATTA
AAAATATTTGTATGGAGGGTATTCATGACTAAAAAGAAATATGGATTAAA
ATTATCAACAGTTCGAAAGTTAGAAGATGAGTTGTGTGATTATCCTAATT
ATCATAAGCAACTCGAAGATTTAAGAAGTGAAATAATGACACCATGGATT
CCAACAGATACAAATATAGGCGGGAGTTTGTACCGTCTAATACATCGAA
AACAGAAATGGCAGTAACTAATTATCTTTGTAGTATACGAAGAGGTAAAA
TCCTTGAGTTTAAGAGCGCTATTGAACGTATAATCAACACATCAAGTAGG
AAAGAACGCGAATTCATTCAAGAGTATTATTTTAATAAAAAGGAATTAGT
GAAAGTTTGTGATGACATACACATTTCTGATAGAACTGCTCATAGAATCA
AAAGGAAAATCATATCTAGATTGGCGGAAGAGTTAGGGGAAGAGTGAAAT
```

TGGCAGTAAAGTGGCAGTTTTTGATACCTAAAATGAGATATTATGATAGT
GTAGGATATTGACTATCTTACTGCGTTTCCCTTATCGCAATTAGGAATAA
AGGATCTATGTGGGTTGGCTGATTATAGCCAATCCTTTTTTAATTTTAAA
AAGCGTATAGCGCGAGAGTTGGTGGTAAATGAA
[[ATGAACGAAAAACAAAAGAGATTCGCAGATGAATATATAATGAATGGA
TGTAATGGTAAAAAAGCAGCAATTTCAGCAGGTTATAGTAAGAAAACAGC
AGAGTCTTTAGCAAGTCGATTGTTAAGGAAATGTTAATGTTTCGGAATAT
TTAAAGAACGATTAGAACAGATACAAGAAGAGCGTTTAATGAGCATTACA
GAAGCTTTAGCGTTATCTGCTTCTATTGCTAGAGGAGAACCTCAAGAGGC
TTACAGTAAGAAATATGACCATTTAAACGATGAAGTGGAAAAAGAGGTTA
CTTACACAATCACACCAACTTTTGAAGAGCGTCAGAGATCTATTGACCAC
ATACTAAAAGTTCATGGTGCGTATATCGACAAAAAAGAAATTACTCAGAA
GAATATTGAGATTAATATTGGTGAGTACGATGACGAAAGTTAA]]ATTAA
ACTTTAACAAACCATCTAATGTTTTCAACAGAAACATATTCGAAATACTA
ACCAATTACGATAACTTCACTGAAGTACATTACGGTGGAGGTTCGAGTGG
TAAGTCTCACGGCGTTATACAAAAAGTTGTACTTAAAGCATTGCAAGACT
GGAAATATCCTAGGCGTATACTATGGCTTAGAAAAGTCCAATCAACAATT
AAAGATAGTTTATTCGAAGATGTCAAAGATTGTTTGATAAACTTCGGTAT
TTGGGACATGTGCCTTTGGAATAAGACTGATAACAAAGTTGAATTGCCAA
ACGGCGCAGTTTTTTGTTTAAAGATTAGATAACCCAGAGAAAATAAAG
TCGATAAAAGGCATATCAGACATAGTCATGGAAGAAGCGTCTGAATTCAC
ACTAAATGATTACACGCAATTAACGTTGCGTTTGAGGGAGCGTAAACACG
TGAATAAGCAAATATTTTTGATGTTTAACCCAGTATCTAAACTGAATTGG
GTTTATAAGTATTTCTTTGAACATGGTGAACAGTGATGAAAATGTCATGAT
TAGACAATCTAGTTATCGAGATAATAAGTTTCTTGATGAAATGACACGAC
AAAACTTAGAGTTGTTAGCAAATCGTAATCCAGCATATTACAAAATTTAT
GCGTTAGGTGAATTTTCTACACTAGACAAATTGGTTTTCCCTAAGTATGA
AAAACGTTTAATAAATAAAGATGAGTTAAGACATTTACCTTCTTATTTTG
GATTGGACTTTGGCTACGTTAATGATCCTAGTGCTTTTTATACATTCTAAA
ATAGATGTAAAGAAAAAGAAGTTATACATCATTGAAGAGTATGTTAAACA
AGGTATGCTGAATGATGAAATAGCTAATGTCATAAAGCAACTTGGTTATG
CTAAAGAAGAAATTACAGCAGATAGTGCAGACAAAAAAGTATAGCTGAA
TTAAGGAATCTAGGGCTTAAAAGGATTTTACCAACCAAAAAGGGAAGGG
CTCGGTTGTACAAGGGTTACAATTCTTAATGCAATTTGAAATCATTGTTG
ATGAACGTTGTTTCAAGACTATTGAAGAGTTTGACAACTACACATGGCAA
AAGGACAAAGATACAGGTGAATATACCAATGAACCAGTAGATACATCAA
TCATTGTATCGATTCGTTGCGTTATTCAGTGGAACGATTC

SEQ ID NO: 5
pGW80A0001 Full Sequence
GGCGCCATGGTTAAGGGCCCTTTGCGAAAGAGTTAGTAAGTTAACAGAA
GACGAACCAAAACTAAATGGTTTAGCAGGAAACTTAGATAAAAAATGAA
TCCAGAATTATATTCAGAACAGGAACAGCAACAAGAACAACAAAAGAATC
AAAAACGAGATAGAGGTATGCACTTATAGAACATCCATTTATGCCGAGAA
AACTTATTGGTTGGAATGGGTAATCTGTGTTAGCTAACTTGTTAGCGAGTTG
GTTGGACTTGAATTGGGATTAATCCCAAGAAAGTACCAACTCAACAACAC
ATAAAGCCCTGTAGGTTCCGACCAATAAGGAAATTGGAATAAAGCAATAA
AAGGAGTTGAAGAAATGAAATTCAGAGAAGCCTTTGAGAATTTTATAACA
AGTAAGTATGTACTTGGTGTTTTAGTAGTCTTAACTGTTTACCAGATAAT
ACAAATGCTTAAATAAAAAAGACTTGATCTGATTAGACCAAATCTTTTG
ATAGTGTTATATTAATAACAAAATAAAAAGGAGTCGCTCACGCCCTACCA
AAGTTTGTGAACGACATCATTCAAAGAAAAAAACACTGAGTTGTTTTAT
AATCTTGTATATTTAGATATTAAACGATATTTAAATATACATCAAGATAT
ATATTTGGGTGAGCGATTACTTAAACGAAATTGAGATTAAGGAGTCGATT
TTTTATGTATAAAAACAATCATGCAAATCATTCAAATCATTTGGAAAATC
ACGATTTAGACAATTTTCTAAAACCGGCTACTCTAATAGCCGGTTGGAC
GCAGATACTGTGTGCATATCTGATCCAAAATTAAGTTTTGATGCAATGAC
GATCGTTGGAAATCTCAACCGAGACAACGCTCAGGCCCTTTCTAAATTA
TGAGTGTAGAGCCCAAATAAGACTTTGGGATATTCTTCAAACAAAGTTT
AAAGCTAAAGCACTTCAAGAAAAGTTTATATTGAATATGACAAAGTGAA
AGCAGATAGTTGGGATAGACGTAAATATGCGTATTGAATTTAATCCAAACA
AACTTACACGAGATGAAATGATTTGGTTAAAACAAAATATAATAAGCTAC
ATGGAAGATGACGGTTTTACAAGATTAGATTTAGCCTTTGATTTTGAAGA
TGATTTGAGTGACTACTATGCAATGTCTGATAAAGCAGTTAAGAAAGTA
TTTTTTATGGTCGTAATGGTAAGCCAGAAACAAATATTTTGGCGTGAGA
GATAGTAATAGATTTATTAAACGATATTTAATAAAAAAGCAAGAATCGTA
TAATGCAGATGCTGAAGTTATGTCTGAACATTTATGGCGTCTAGAAATCG
AACTTAAAGAGATATGGTGGATTACTGGAATGATTGCTTTAGTGATTTA
CATATCTTGCAACCAGATTGGAAAACTATCCAACGCACTGCGGATAGAGC
AATAGTTTTATCTTATTGAGTGATGAAGAAGAATGGGGAAAGCTTCACA
GAAATTCTAGAACAAAATATAAGATTTGATAAAAGAAGAATTTCGCCAGTC
GATTTAACGGACTTAATGAAATCGACTTTAAAAGCGAACGAAAAACAATT
GCAAAAACAAATCGATTTTTGGCAACATGAATTTAAATTTTGGAAATAGT
GTACATATTAATATTACTGAACAAAAATGATATATTTAAACTATTCTAAT
TTAGGAGGATTTTTTTATGAAGTGTCTATTTAAAAATTTGGGGAATTTAT
ATGAGGTCAAAGAATAATTTACCCCTATAAACTTTAGCCACCTCAAGTAA
AGAGGTAAAATTGTTAGTTTATATAAAAAATTTAAAGGTTTGTTTTATA GCGTTTTATTTTGGCTTTGTATTCTTTCATTTTTTAGTGTATTAAATGAA
ATGGTTTTAAATGTTTCTTTACCTGATATTGCAAATCATTTTAATACTAC
TCCTGGAATTACAAACTGGGTAAACACTGCATATATGTTAACTTTTTCGA
TAGGAACAGCAGTATATGGAAAATTATCTGATTATATAAATATAAAAAAA
TTGTTAATTATTGGTATTAGTTTGAGCTGTCTTGGTCATTGATTGCTTT
TATTGGGCCCACCTAGGCAAATATGCTCTTACGTGCTATTATTTAAGTGA
CTATTTAAAAGGAGTTAATAAATATGCGGCAAGGTATTCTTAAATAAACT
GTCAATTTGATAGCGGGAACAAATATTAGATGTCCTTTTTTAGGAGGGG
TTAGTTTTTTGTACCCAGTTTAAGAATACCTTTATCATGTGATTCTAAAG
TATCCAGAGAATATCTGTATGCTTTGTATACCTATGGTTATGCATAAAAA
TCCCAGTGATAAAAGTATTTATCACTGGGATTTTTATGCCCTTTTGGGTT
TTTGAATGGAGGAAAATCACATGAAAATTATTAATATTGGAGTTTTAGCT
CATGTTGATGCAGGAAAAACTACCTTAACAGAAAGCTTATTATATAACAG
TGGAGCGATTACAGAATTAGGAAGCGTGGACAAAGGTACAACGAGGACGG
ATAATACGCTTTTAGAACGTCAGAGAGGAATTACAATTCAGACAGGAATA
ACCTCTTTTCAGTGGGAAAATACGAAGGTGAACATCATAGACACGCCAGG
ACATATGGATTTCTTAGCAGAAGTATATCGTTCATTATCAGTTTTAGATG
GGGCAATTCTACTGATTTCTGCAAAAGATGGCGTACAAGCACAAACTCGT
ATATTATTTCATGCACTTAGGAAAATGGGGATTCCCACAATCTTTTTTAT
CAATAAGTTGACCAAAATGGAATTGATTTATCAACGGTTTATCAGGATA
TTAAAGAGAAACTTTCTGCCGAAATTGTAATCAAACAGAAGGTAGAACTG
TATCCTAATATGTGTGTGACGAACTTTACCGAATCTGAACAATGGGATAC
GGTAATAGGGGAAACGATAACCTTTTAGAGAAATATATGTCCGGTAAAT
CATTAGAAGCATTGGAACTCGAACAAGGAAAGCATAAGATTTCAGAT
TGTTCTCTGTTCCCTCTTTATCATGGAAGTGCAAAAAGTAATATAGGGAT
TGATAACCTTATAGAAGTTATTACTAATAAATTTTATTCATCAACACATC
GAGGTCCGTCTGAACTTTGCGGAAATGTTTTCAAAATTGAATATACAAAA
AAAAGACAACGTCTTGCATATACGCCTTTATAGTGGAGTACTACATTT
ACGAGATTCGGTTAGAGTATCAGAAAAAGAAAAATAAAAGTTACAGAAGA
TGTATACTTCAATAAATGGTGAATTATGTAAGATTGATAGAGCTTATTCT
GGAGAAATTGTTATTTTGCAAAATGAGTTTTTGAAGTTAAATAGTGTTCT
TGGAGATACAAACTATTGCCACAGAGAAAAAGATTGAAAATCCGCACC
CTCTACTACAAACAACTGTTGAACCGAGTAAACCTGAACAGAGAGAAATG
TTGCTTGATGCCCTTTTGGAAATCTCAGATAGTGATCCGCTTCTACGATA
TTACGTGGATTGTACGACACATGAAATTATACTTTCTTTCTTAGGGAAAG
TACAAATGGAGTGATTAGTGCACTGTTGCAAGAAAGTATCATGTGGAG
ATAGAACTAAAAGAGCCTACAGTCATTTATATGGAGAGACCGTTAAAAAA
TGCAGAATATACCATTCACATCGAAGTGCCGCAAATCCTTTCTGGGCTT
CCATTGGTTATCTGTATCGCCGCTTCCGTTGGGAAGTGGAATGCAGTAT
GAGAGCTCGGTTTCTCTTGGATACTTAAATCAATCATTTCAAAATGCAGT
TATGGAAGGGGTACGCTATGGTTGCGAACAAGGATTATATGGTTGGAATG
TGACGGATTGTAAAATCTGTTTTAAGTACGGTTTATACTATAGCCCTGTT
AGTACTCCAGCAGATTTTCGGATGCTTACTCCTATTGTACTGGAGCAAGC
CTTTAGAAAAGCTGGAACAGAATTGTTAGAGCCATATCTTAGTTTTAAAG
TTTATGCACCACAGGAAATATCTTTCACGGGCATATAACGATGCTCCCAA
TATTGTGCAAATATCGTAAATACTCAACTGAAAAATAATGAGGTCATTAT
TATTGGAGAAATTCCTGCTCGATGTATTCAAGATTATCGCAATGATTTAA
CTTTTTTTACAAATGGGCTTAGTGTTTGTTTAGCAGAGCTAAAAGGATAT
CAGGTTACCACTGGCAACCGTGTTTGCCAGACCCGTCGTCTAAATAGTCG
GATAGATAAAGTAAGATATATGTTCAATAAAATAACTTAGTGCGTTTTAT
GTTGTTATATAAATATGGTTTCTTATTAAATAAGATGAAATATTCTTTAA
TATAGATTTTGAATTAAAGTGGAAAGGAGGAGATTGTTATTATAAACTACA
AGTGGATATTGTCCTAGTTGTGAAATAAAACAAGCACTACGAATACGA
GTGGATACTATACTTAAAAATTTCCCTTTATACAGCCCAAATGTAAGAA
CGAAACTTTAATTAATGTTCAAAAAATGAATATAATAACAATCAAAGAGC
CAGACGCCAAGACGCAGAGCCGATAATTTGAGAAATGAAACTCTCATCTT
ATCGGCTCTTTTGTTTATCTGAAATTTACTGACTAGCCTTCAATATTTC
CGCGGCCAGCTTACTATGCCATTATTAAGCTTGTAATATCGGAGGGTTTA
TTAATTGGCAGTAAAGTGGCAGTTTTTGATACCTTAAATGAGATATTATG
ATAGTGTAGGATATTGACTATCGTACTGCGTTTCCCTACCGCAAATTAGG
AATAAAGGATCTATGTGGGTTGGCTGATTATAGCCAATCCTTTTTTAATT
TTAAAAGCGTATAGCGCGAGAGTTGGTGGTAAATGAAATGAACGAAAA
CAAAAGAGATTCGCAGATGAATATATAATGAATGGATGTAATGGTAAAA
AGCAGCAATTACAGTAGGTTATAGTAAGAAAACAGCAGAGTCTTTAGCAA
GTCGATTGTTAAGAAATGTTAATGTTTCGGAATATATTAAAGAACGATTA
GAACAGGTACAAGAAGAGCGTTTAATGAGTCATTACGAAGCTTTAGCGTT
ATCTGCTTCTATTGCTAGAGGAGAACCTCAAGAGGCTTACAGTAAGAAAT
ATGACCATTTAAACGATGAAGTGGAAAAAGAGGTTACTTACACAATCACA
CCAACTTTTGAAGAGCGTCAGAGATCTATTGACCACATACTAAAAGTACA
TGGTGCGTATATCGATAAAAAAGAAATTACTCAGAAGAATATTGAGATTA
ATATTGGTGAGTACGATGACGAAAGTTAATTGAGATTAACAAACCGTC
TAATGTTTTCAATAGCCGCGGGGGCCCAACGAGCGGCCGCATAGTTAAGCCAGCCCCGACACCCGCC
AACACCCGCTGACGCGCCCTGACGGGCTTGTCTGCTCCCGGCATCCGCTT

SEQUENCES

```
ACAGACAAGCTGTGACCGTCTCCGGGAGCTGCATGTGTCAGAGGTTTTCA
CCGTCATCACCGAAACGCGCGAGACGAAAGGGCCTCGTGATACGCCTATT
TTTATAGGTTAATGTCATGATAATAATGGTTTCTTAGACGTCAGGTGGCA
CTTTTCGGGGAAATGTGCGCGAACCCCTATTTGTTTATTTTTCTAAATA
CATTCAAATATGTATCCGCTCATGAGACAATAACCCTGATAAATGCTTCA
ATAATATTGAAAAGGAAGAGTATGAGTATTCAACATTTCCGTGTCGCCC
TTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCC
CCGAAGAACGTTTTCCAATGATGAGCACTTTTAAAGTTCTGCTATGTGGC
GCGGTATTATCCCGTATTGACGCCGGGCAAGAGCAACTCGGTCGCCGCAT
ACACTATTCTCAGAATGACTTGGTTGAGTACTCACCGGTCACAGAAAAGC
ATCTTACGGATGGCATGACAGTAAGAGAATTATGCAGTGCTGCCATAACC
ATGAGTGATAACACTGCGGCCAACTTACTTCTGACAACGATCGGAGGACC
GAAGGAGCTAACCGCTTTTTTGCACAACATGGGGGATCATGTAACTCGCC
TTGATCGTTGGGAACCGGAGCTGAATGAAGCCATACCAAACGACGAGCGT
GACACCACGATGCCTGTAGCAATGGCAACAACGTTGCGCAAACTATTAAC
TGGCGAACTACTTACTCTAGCTTCCCGGCAACAATTAATAGACTGGATGG
AGGCGGATAAAGTTGCAGGACCACTTCTGCGCTCGGCCCTTCCGGCTGGC
TGGTTTATTGCTGATAAATCTGGAGCCGGTGAGCGTGGGTCTCGCGGTAT
CATTGCAGCACTGGGGCCAGATGGTAAGCCCTCCCGTATCGTAGTTATCT
ACACGACGGGGAGTCAGGCAACTATGGATGAACGAAATAGACAGATCGCT
GAGATAGGTGCCTCACTGATTAAGCATTGGTAACTGTCAGACCAAGTTTA
CTCATATATACTTTAGATTGATTTAAAACTTCATTTTTAATTTAAAAGGA
TCTAGGTGAAGATCCTTTTTGATAATCTCATGACCAAAATCCCTTAACGT
GAGTTTTCGTTCCACTGAGCGTCAGACCCCGTAGAAAAGATCAAAGGATC
TTCTTGAGATCCTTTTTTTCTGCGCGTAATCTGCTGCTTGCAAACAAAAA
AACCACCGCTACCAGCGGTGGTTTTTTTGCCGGATCAAGAGCTACCAACT
CTTTTTTCCGAAGGTAACTGGCTTCAGCAGAGCGCAGATACCAAATACTGT
TCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGT
GGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCT
TGGAGCGAACGACCTACACCGAACCTGAGATACCTACAGCGTGAGCTATG
AGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAAC
GCCTGGTATCTTTATAGTCCTGTCGGGTTTCGCCACCTGTGACTTGAGCG
TCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCAC
ATGTTCTTTCCTGCGTTATCCCCTGATTCTGTGGATAACGTATTACCGC
CTTTGAGTGAGCTGGCGGGTCTAGTTAATGTGAACGTAACATTAGCTAG
ATTTTTTTATTCAAAAATATTTACAAATATTAGGAAATTTAAGTGTAA
AAGAGTTGATAAATGATTATATTGGGACTATAATATAATTAAGGTCGATT
GAATTCGTTAACTAATTAATCACCAAAAAGGAATAGAGTATGAAGTTTGG
AAATATTTGTTTTCGTATCAACCACCAGGTGAACTCATAAGCAAGTAA
TGGATCGCTTTGTTCGGCTTGGTATCGCCTCAGAAGAGGTAGGGTTTGAT
ACATATTGGACCTTAGAACATCATTTTACAGAGTTTGGTCTTACGGGAAA
TTTATTTGTTGCTGCGGCTAACCTGTTAGGAAGAACTAAAACATTAAATG
TTGGCACTATGGGGGTTGTTATTCCGACAGCACACCCAGTTCGACAGTTA
GAAGACGTTTTATTATTAGATCAAATGTCGAAAGGTCGTTTTAATTTTGG
AACCGTTCGAGGGCTATACCATAAAGATTTTCGAGTATTTGGTGTTGATA
TGGAAGAGTCTCGAGCAATTACTCAAATTTCTACCAGATGATAATGGAA
AGCTTACAGACAGGAACCATTAGCTCTGATAGTGATTACATTCAATTTCC
TAAGGTTGATGTATATCCCAAAGTGTACTCAAAAATGTACCAACCTGTA
TGACTGCTGAGTCCGCAAGTACGACAGAATGGCTAGCAATACAAGGGCTA
CCAATGGTTCTTAGTTGGATTATTGGTACTAATGAAAAAAAAGCACAGAT
GGAACTCTATAATGAAATTGCGACAGAATATGGTCATGATATATCTAAAA
TAGATCATTGTATGACTTATATTTGTTCTGTTGATGATGCACAAAAG
GCGCAAGATGTTTGTCGGGAGTTTCTGAAAAATTGGTATGACTCATATGT
AAATGCGACCAATATCTTTAATGATAGCAATCAAACTCGTGGTTATGATT
ATCATAAAGGTCAATGGCGTGATTTTGTTTTACAAGGACATACAAACACC
AATCGACGTGTTGATTATAGCAATGGTATTAACCCCGTAGGCACTCCTGA
GCAGTGTATTGAAATCATTCAACGTGATATTGATGCAACGGGTATTACAA
ACATTACATGCGGATTTGAAGCTAATGGAACTGAAGATGAAATAATTGCT
TCCATGCGACGCTTTATGACACAAGTCGCTCCTTTCTTAAAAGAACCTAA
ATAAATTACTTATTTGATACTAGAGATAATAAGGAACAAGTTATGAAATT
TGGATTATTTTTCTAAACTTTCAGAAAGATGGAATAACATCTGAAGAAA
CGTTGGGATAATATGGTAAAGACTGTCACGTTAATTGATTCAACTAAATAT
CATTTTAATACTGCCTTTGTTAATGAACATCACTTTTCAAAAAATGGTAT
TGTTGGAGCACCTATTACCGCAGCTGGTTTTTTATTAGGGTTAACAAATA
AATTACATATTGGTTTCATTAAATCAAGTAATTACCACCCATCACCCTGTA
CGTGTAGCAGAAGAAGCCAGTTTATTAGATCAAATGTCAGAGGGACGCTT
CATTCTTGGTTTAGTGACTGCGAAAGTGATTTCGAAATGGAATTTTTA
GACGTCATATCTCATCAAGGCAACAACAATTTGAAGCATGCTATGAAATA
ATTAATGACGCAGTTGTCATTATTGGCCATCCCCAAACGCACTTTA
TGATTTTCCAAAGGTTTCAATTAATCCACACTGTTTACAGTGAGAATGGAC
CTAAGCAATATGTATCCGCTACATCAAAAGAAGTCGTCATGTGGGCAGCG
AAAAAGGCACTGCCTTTAACGTTTAAGTGGGAGGATAATTTAGAAACCAA
AGAACGCTATGACATTTGCTATATAATAAACAGCACAACAATATGGTATTG
ATATTTCGGATGTTGATCATCAATTAACTGTAATTGCGAACTTAAATGCT
GATAGAAGTACGGCTCAAGAAGTGAGAGAATACTTAAAAGACTATAT
CACTGAAACTTACCCTCAAATGGACAGAGATGAAAAAATTAACTGCATTA
TTGAAGAGAATGCAGTTGGGTCTCATGATGCTATTATGAATCGACAAAA
TTAGCAGTGGAAAACAGGGTCTAAAATATTTTATTATCCTTTGAATC
AATGTCCGATATTAAAGATGTAAAGATATTATTGATATGTTGAACAAA
AAATCGAAATGAATTTACCATAATAAATTAAAGGCAATTTCTATATTAG
ATTGCCTTTTTGGCGCGCCTATTCTAATGCATAATAAATACTGATAACAT
CTTATATTTTGTATTATATTTGTATTATCGTTGACATGTATAATTTTGA
TATCAAAACTGATTTTCCCTCTATTATTTTCGAGATTTATTTTCTTAAT
TCTCTTTAACAAACTAGAAATATTGTATATACAAAAATTATAATAATA
GATGAATAGTTTAATTATAGGTGTTCATCAATCGAAAAAGCAACGTATCT
TATTTAAAGTGCGTTGCTTTTTTCTCATTTATAAGGTTAAATAATTCTCA
TATATCAAGCAAAGTGACA
```

What is claimed:

1. A growth-independent method for detecting a microorganism of interest in a sample, comprising:
   contacting the sample with a plurality of non-replicative transduction particles (NRTPs), wherein the plurality of NRTPs are produced using a silent mutation/complementation method or a deletion/complementation method, wherein said methods do not produce NRTPs that contain a viral genome, such that the plurality of NRTPs transduces one or more microorganisms of interest in the sample, wherein the plurality of NRTPs comprises a reporter nucleic acid sequence, and wherein the growth rate of the one or more microorganisms of interest is less than logarithmic phase;
   providing conditions for activation of the reporter nucleic acid sequence; and
   detecting a signal produced by the reporter nucleic acid sequence, wherein the presence of the signal indicates the presence of the one or more microorganisms of interest, and wherein the absence of the signal indicates the absence of the one or more microorganisms of interest.

2. The method of claim 1, further comprising providing an antimicrobial agent to the sample and detecting the signal produced by the reporter nucleic acid sequence to determine whether the one or more microorganisms of interest is susceptible or non-susceptible to the antimicrobial agent.

3. The method of claim 1, wherein the one or more microorganisms of interest is in stationary phase; or wherein the one or more microorganisms of interest is undergoing no growth.

4. The method of claim 1, wherein the one or more microorganisms of interest comprises a Methicillin Resistant *Staphylococcus aureus* (MRSA) cell, *Staphylococcus aureus*, *Staphylococcus* spp., *Enterobacteriaceae*, *Enterococcus* spp. *Streptococcus* spp., *Acinetobacter* spp., or *Pseudomonas* spp.

5. The method of claim 1, wherein the sample is a clinical sample.

6. The method of claim 1, wherein the signal is a luminescence signal; or wherein the detecting step comprises measuring the relative light units (RLU) emitted by the signal.

7. The method of claim 1, wherein the providing step comprises contacting the sample with a fatty aldehyde bacterial luciferase substrate reagent, optionally wherein the reagent is tridecanal.

8. The method of claim 2, wherein the antimicrobial agent is cefoxitin, a β-lactam, an extended-spectrum β-lactam, an Aminoglycoside, an Ansamycin, a Carbacephem, Carbapenems, any generation of Cephalosporin, a Glycopeptide, a Lincosamide, a Lipopeptide, a Macrolide, a Monobactam, a Nitrofuran, an Oxazolidonone, a Penicillin, a Polypeptide, a Quinolone, a Fluoroquinolone, a Streptogramin, a Sulfonamide, a Tetracycline, a Rifampicin, a mycobacterial antibiotic, Chloramphenicol, and/or Mupirocin.

9. The method of claim 1, wherein the reporter nucleic acid sequence encodes a detectable or selectable marker.

10. The method of claim 1, wherein the signal can be detected at a limit of detection (LoD) of less than 1-1000, 1-5, 5-10, 10-100, 100-1000, 10, 100, 1,000 colony forming units (CFU).

11. The method of claim 1, further comprising providing varying pre-determined concentrations of antibiotic to the sample and detecting the amount of the signal to determine the minimum inhibitory concentration of the one or more microorganisms of interest to the antibiotic.

* * * * *